US011427833B2

(12) United States Patent
Machida et al.

(10) Patent No.: US 11,427,833 B2
(45) Date of Patent: Aug. 30, 2022

(54) PEPTIDE EFFECTIVE IN CONTROL OF GEMINIVIRUS DISEASE AND USE THEREOF

(71) Applicant: ISHIHARA SANGYO KAISHA, LTD., Osaka (JP)

(72) Inventors: Yasunori Machida, Aichi (JP); Norifusa Matsuo, Osaka (JP); Masato Omatsu, Osaka (JP); Takanori Suzuki, Osaka (JP); Mika Tanaka, Osaka (JP)

(73) Assignee: ISHIHARA SANGYO KAISHA, LTD., Osaka (JP)

( * ) Notice: Subject to any disclaimer, the term of this patent is extended or adjusted under 35 U.S.C. 154(b) by 0 days.

(21) Appl. No.: 16/318,990

(22) PCT Filed: Jul. 20, 2017

(86) PCT No.: PCT/JP2017/026196
§ 371 (c)(1),
(2) Date: Jan. 18, 2019

(87) PCT Pub. No.: WO2018/016556
PCT Pub. Date: Jan. 25, 2018

(65) Prior Publication Data
US 2019/0300584 A1 Oct. 3, 2019

(30) Foreign Application Priority Data
Jul. 21, 2016 (JP) ............................ JP2016-143695

(51) Int. Cl.
*C12N 15/82* (2006.01)
*A01H 6/82* (2018.01)
*A01H 6/60* (2018.01)
*A01H 6/20* (2018.01)
*A01H 6/54* (2018.01)
*C07K 14/415* (2006.01)
*C12N 7/00* (2006.01)
*C12N 15/09* (2006.01)

(52) U.S. Cl.
CPC ........... *C12N 15/8283* (2013.01); *A01H 6/20* (2018.05); *A01H 6/54* (2018.05); *A01H 6/60* (2018.05); *A01H 6/82* (2018.05); *C07K 14/415* (2013.01); *C12N 7/00* (2013.01); *C12N 15/09* (2013.01); *C12N 15/82* (2013.01)

(58) Field of Classification Search
None
See application file for complete search history.

(56) References Cited

U.S. PATENT DOCUMENTS 7,361,749 B2 4/2008 Alexandrov et al.
8,853,493 B2 * 10/2014 Ye ..................... C12N 15/8261 800/290
9,000,140 B2 4/2015 Alexandrov et al.
2006/0031960 A1 2/2006 Alexandrov et al.
2006/0037098 A1 2/2006 Alexandrov et al.
2006/0084796 A1 4/2006 Alexandrov et al.
2006/0194958 A1 8/2006 Alexandrov et al.
2006/0194959 A1 8/2006 Alexandrov et al.
2006/0199952 A1 9/2006 Alexandrov et al.
2006/0206954 A1 9/2006 Alexandrov et al.
2006/0211852 A1 9/2006 Alexandrov et al.
2006/0211853 A1 9/2006 Alexandrov et al.
2006/0211854 A1 9/2006 Alexandrov et al.
2006/0212962 A1 9/2006 Alexandrov et al.
2006/0212963 A1 9/2006 Alexandrov et al.
2006/0217539 A1 9/2006 Alexandrov et al.
2006/0217540 A1 9/2006 Alexandrov et al.
2006/0217541 A1 9/2006 Alexandrov et al.
2006/0217542 A1 9/2006 Alexandrov et al.
2006/0217543 A1 9/2006 Alexandrov et al.
2006/0217544 A1 9/2006 Alexandrov et al.
2006/0217545 A1 9/2006 Alexandrov et al.
2006/0229442 A1 10/2006 Alexandrov et al.
(Continued)

FOREIGN PATENT DOCUMENTS

EP 1033405 A2 9/2000
EP 1586645 A2 10/2005
(Continued)

OTHER PUBLICATIONS

Theodoris et al, PNAS, 100 (11): 6837-6842, May 2003 (Year: 2003).*
Shen et al., "Tabacco RING E3 Ligase NtRFP1 Mediates Ubiquitination and Proteasomal Degradation of a Geminivirus-Encoded BC1", Molecular Plant, vol. 9, No. 6, 2016, pp. 911-925.
(Continued)

*Primary Examiner* — Elizabeth F McElwain
(74) *Attorney, Agent, or Firm* — Greenblum & Bernstein, P.L.C.

(57) ABSTRACT

Disclosed are a decoy peptide which is a partial peptide of ASYMMETRIC LEAVES1 (AS1), the decoy peptide being capable of interacting with βC1 encoded by a betasatellite of a virus belonging to the family Geminiviridae, a nucleic acid encoding the decoy peptide, an expression vector comprising the nucleic acid, a geminivirus disease control agent comprising the decoy peptide or the nucleic acid, a method for controlling a geminivirus disease using the geminivirus disease control agent, a transgenic plant into which the nucleic acid is introduced, and a method for reducing a disease symptom caused by a virus that comprises βC1 and belongs to the family Geminiviridae, using the nucleic acid. Also disclosed is a method for evaluating the degree of reduction in a disease symptom caused by a virus that comprises βC1 and belongs to the family Geminiviridae.

6 Claims, 9 Drawing Sheets

Specification includes a Sequence Listing.

(56) References Cited

U.S. PATENT DOCUMENTS

| | | | |
|---|---|---|---|
| 2006/0229443 | A1 | 10/2006 | Alexandrov et al. |
| 2006/0235217 | A1 | 10/2006 | Alexandrov et al. |
| 2006/0235218 | A1 | 10/2006 | Alexandrov et al. |
| 2006/0252920 | A1 | 11/2006 | Alexandrov et al. |
| 2006/0270842 | A1 | 11/2006 | Alexandrov et al. |
| 2006/0281909 | A1 | 12/2006 | Alexandrov et al. |
| 2007/0179287 | A1 | 8/2007 | Alexandrov et al. |
| 2009/0182122 | A1 | 7/2009 | Alexandrov et al. |
| 2009/0203891 | A1 | 8/2009 | Alexandrov et al. |
| 2011/0028704 | A1 | 2/2011 | Alexandrov et al. |
| 2012/0077968 | A1 | 3/2012 | Alexandrov et al. |
| 2013/0102767 | A1 | 4/2013 | Alexandrov et al. |
| 2014/0058075 | A1 | 2/2014 | Alexandrov et al. |
| 2014/0288287 | A1 | 9/2014 | Alexandrov et al. |
| 2015/0057441 | A1 | 2/2015 | Alexandrov et al. |
| 2015/0112052 | A1 | 4/2015 | Alexandrov et al. |
| 2016/0076046 | A1 | 3/2016 | Alexandrov et al. |
| 2017/0037426 | A1 | 2/2017 | Alexandrov et al. |

FOREIGN PATENT DOCUMENTS

| | | | |
|---|---|---|---|
| JP | 2003-167883 | A | 6/2003 |
| JP | 2005-291742 | A | 10/2005 |
| JP | 2007-181453 | A | 7/2007 |

OTHER PUBLICATIONS

Theodoris et al., "Conservation and molecular dissection of Rough Sheath2 and Asymmetric Leaves1 function in leaf development", PNAS, vol. 100, No. 11, 2003, pp. 6837-6842.

Yang et al., "BC1, the pathogenicity factor of TYLCCNV, interacts with AS1 to alter leaf development and suppress selective jasmonic acid responses", Genes and Development, vol. 22, 2008, pp. 2564-2577.

Sharma et al., "RNAi mediated broad-spectrum transgenic resistance in Nicotiana benthamiana to chilli-infecting begomoviruses", Plant cell reports, vol. 34, No. 8, 2015, pp. 1389-1399.

International Search Report in International Patent Application No. PCT/JP2017/026196, dated Sep. 5, 2017, along with an English translation thereof.

* cited by examiner

Statistical significance was determined by Dunnett's multiple comparison test.
n=20, *p<0.05 compared with the vector control.

PEPTIDE EFFECTIVE IN CONTROL OF GEMINIVIRUS DISEASE AND USE THEREOF

SEQUENCE LISTING

The instant application contains a Sequence Listing which has been filed electronically in ASCII format and is hereby incorporated by reference in its entirety. Said ASCII copy, created on Jun. 3, 2019, is named P56979_SL.txt and is 50,187 bytes in size.

TECHNICAL FIELD

The present invention relates to a peptide that suppresses the function of pathogenicity protein βC1 of geminiviruses, a nucleic acid encoding the peptide, an expression vector comprising the nucleic acid, a geminivirus disease control agent comprising the peptide or the nucleic acid, a method for controlling a geminivirus disease using the geminivirus disease control agent, and a transgenic plant into which the nucleic acid is introduced. The present invention also relates to a method for reducing a disease symptom caused by a virus that comprises βC1 and belongs to the family Geminiviridae, using the nucleic acid.

Further, the present invention relates to a method for evaluating the degree of reduction in a disease symptom caused by a virus that comprises βC1 and belongs to the family Geminiviridae.

BACKGROUND ART

Plant viruses induce various disease symptoms in host plants. In crops that develop leaf curl symptoms, which are typical disease symptoms, their yields are reduced, and thus plant virus diseases result in economic losses. To control plant virus diseases, crops are physically separated from virus-mediated insects or virus-infected plants using, for example, a net; or chemical pesticides, resistant cultivars, etc., are used. However, the effects obtained by these methods vary depending on virus species, and there are many virus species that have never been controlled completely.

Geminiviruses, which are a viral group including many difficult-to-control viruses, such as Tomato yellow leaf curl virus (TYLCV) and Cotton leaf curl virus (CLCuV), cause significant crop losses worldwide.

Geminivirus disease symptoms are caused by pathogenicity proteins encoded by the genomes of the viruses and betasatellites often accompanying the viruses. The betasatellites encode βC1 protein. The βC1 protein has the activity of suppressing the resistance mechanism of plants (Mubin M et al., (2011) Virol J, 8: 122, Li F et al., (2014) PLoS Pathog, 10(2): e1003921, Ammara U E et al., (2015) Virol J, 12(1): 38). Further, the βC1 protein, even alone, has the activity of causing leaf curl symptoms, and is a highly virulent pathogenicity factor (Cui X et al., (2004) J Virol, 78(24): 13966-74).

The βC1 protein is considered to interact with ASYMMETRIC LEAVES 1 (AS1), which is a transcription factor to regulate leaf development, to inhibit the formation of a complex of the AS1 protein and the ASYMMETRIC LEAVES 2 (AS2) protein, thereby causing leaf curl symptoms (NPL 1). In addition, AS1 is reported to homodimerize through the mediation of the C-terminal domain (CTD) of AS1 (NPL 2).

Thus, technologies for suppressing pathogenicities of βC1 are considered important from the standpoint of the control of virus diseases, and a technology has also been reported which includes βC1 as a target sequence for gene silencing (NPL 3). However, since the βC1 proteins of geminiviruses suppress gene silencing, this technology is imperfect.

There is also a report that disease symptoms caused by βC1 can be reduced by tobacco RING E3 ligase NtRFP1, which mediates ubiquitination and proteasomal degradation of βC1 (NPL 4). However, βC1 has the function of decreasing the activity of proteasome; therefore, this technology is also not perfect as a method of control (Jia et al., (2016) PLoS Pathog, 12(6): e1005668).

As described above, technologies for resistance to pathogenicity factor βC1 are currently insufficient.

CITATION LIST

Non-Patent Literature

NPL 1: Yang J Y et al., (2008) Genes & Development, 22(18), 2564-2577.

NPL 2: Threodoris G et al., (2003) PNAS, 100(11), 6837-6842.

NPL 3: Sharma V K et al., (2015) Plant Cell Reports, 34(8), 1389-1399.

NPL 4: Shen Q et al., (2016) Mol Plant, 9(6), 911-925.

SUMMARY OF INVENTION

Technical Problem

An object of the present invention is to provide a peptide that suppresses the function of pathogenicity protein βC1 of geminiviruses, a nucleic acid encoding the peptide, an expression vector comprising the nucleic acid, a geminivirus disease control agent comprising the peptide or the nucleic acid, a method for controlling a geminivirus disease using the geminivirus disease control agent, and a transgenic plant into which the nucleic acid is introduced. Another object of the present invention is to provide a method for reducing a disease symptom caused by a virus that comprises βC1 and belongs to the family Geminiviridae, using the nucleic acid.

Still another object of the present invention is to provide a method for evaluating the degree of reduction in a disease symptom caused by a virus that comprises βC1 and belongs to the family Geminiviridae, the method enabling the evaluation in a shorter period of time than conventional methods.

Solution to Problem

The present inventors conducted extensive research to achieve the above objects, and found that resistance to βC1 is obtained by providing a partial peptide of AS1, which is a receptor for βC1, as a decoy peptide in a plant.

Those skilled in the art may readily envisage that if excessive receptor AS1 is supplied, the plant would be resistant to βC1. As demonstrated in the Examples described later, however, the results showed that in an experimental group in which the AS1 gene was overexpressed, the disease symptom caused by βC1 was not suppressed, and was rather enhanced.

The inventors further conducted extensive research based on these findings, and accomplished the present invention. The present invention provides, for example, the following decoy peptide, nucleic acid, expression vector, geminivirus disease control agent, method for controlling a geminivirus disease, and transgenic plant.

Item 1. A decoy peptide which is a partial peptide of ASYMMETRIC LEAVES1 (AS1), the decoy peptide being capable of interacting with βC1 encoded by a betasatellite of a virus belonging to the family Geminiviridae.

Item 2. The decoy peptide according to Item 1, wherein the virus belongs to the genus Begomovirus of the family Geminiviridae.

Item 3. The decoy peptide according to Item 1 or 2, wherein the virus is Tomato yellow leaf curl virus, Cotton leaf curl virus, or Ageratum yellow vein virus.

Item 4. The decoy peptide according to any one of Items 1 to 3, wherein the AS1 is derived from a plant belonging to the family Malvaceae, Solanaceae, Brassicaceae, or Fabaceae.

Item 5. The decoy peptide according to any one of Items 1 to 4, wherein the AS1 is derived from cotton, okra, kenaf, mallow, rose of Sharon, Confederate rose, hibiscus, cacao, balsa, jute, durian, Cola, Japanese linden, tomato, peppers, potato, petunia, tobacco plants, rapeseed, soybean, or common bean.

Item 6. The decoy peptide according to any one of Items 1 to 5, which comprises at least one motif selected from the group consisting of a leucine zipper motif, a PSVTL(S/T)L motif (SEQ ID NO: 82), and a coiled-coil motif, and is capable of reducing a disease symptom caused by a virus that comprises βC1 and belongs to the family Geminiviridae.

Item 7. The decoy peptide according to any one of Items 1 to 6, which comprises a coiled-coil motif and is capable of reducing a disease symptom caused by a virus that comprises βC1 and belongs to the family Geminiviridae.

Item 8. A decoy peptide set forth in the following (A) or (B):
(A) a peptide consisting of the amino acid sequence represented by any one of SEQ ID NOs: 1 to 18,
(B) a peptide consisting of the amino acid sequence represented by any one of SEQ ID NOs: 1 to 18 in which 1 to 43 amino acids are deleted, substituted, inserted, and/or added, the peptide being capable of interacting with βC1 encoded by a betasatellite of a virus belonging to the family Geminiviridae.

Item 9. A nucleic acid encoding the decoy peptide according to any one of Items 1 to 8.

Item 10. An expression vector comprising the nucleic acid according to Item 9.

Item 11. A geminivirus disease control agent comprising the decoy peptide according to any one of Items 1 to 8 or the nucleic acid according to Item 9.

Item 12. A method for controlling a geminivirus disease, comprising applying the geminivirus disease control agent according to Item 11.

Item 13. A transgenic plant transformed with the nucleic acid according to Item 9.

Item 14. A method for reducing disease symptom caused by a virus that comprises βC1 and belongs to the family Geminiviridae, the method comprising introducing the nucleic acid according to Item 9 into a plant to transform the plant.

Item 15. A method for evaluating the degree of reduction in a disease symptom caused by a virus that comprises βC1 and belongs to the family Geminiviridae, the method comprising simultaneously introducing βC1 encoded by a betasatellite of a virus belonging to the family Geminiviridae and a decoy peptide capable of interacting with the βC1 into a plant such that the f3C1 and the decoy peptide are transiently expressed.

Advantageous Effects of Invention

The decoy peptide of the present invention makes it possible to suppress disease symptoms of pathogenicity factor βC1 expressed in host plants by geminiviruses. Moreover, in the present invention, problems are relatively less likely to be caused than in conventional technologies, in terms of effect persistence when a mutant viral strain appears, safety, cost, etc.

Further, the method of evaluation of the present invention enables the degree of reduction, in a disease symptom caused by a geminivirus, due to a decoy peptide to be evaluated in an extremely short period of time compared with conventional methods. In addition, the method of evaluation of the present invention allows evaluation of the suppression effect of a decoy peptide on movement of a pathogenicity factor of a geminivirus in a plant.

BRIEF DESCRIPTION OF DRAWINGS

*p<0.05, p<0.01 (comparisons with control)). FIG. 7** (right) shows pictures indicating criteria for the symptom score.

FIG. 8 (right) shows sample pictures of near the upper quartile of each case.

DESCRIPTION OF EMBODIMENTS

Figure 1:
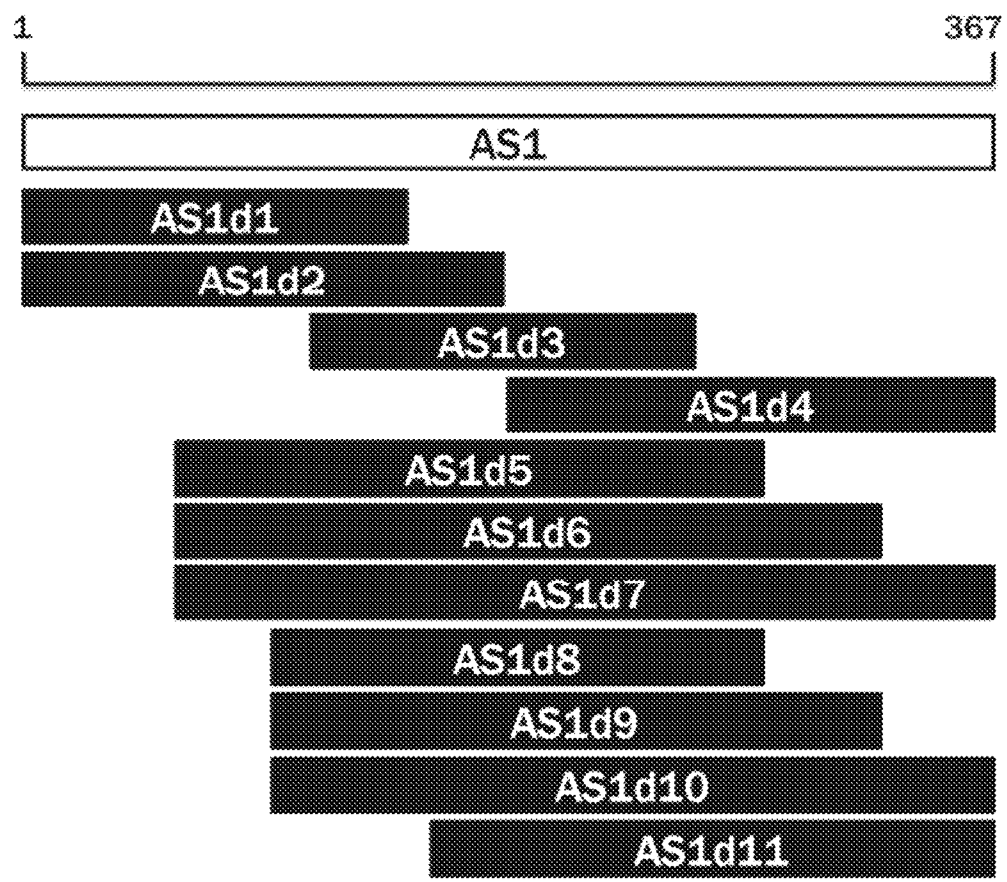
FIG. 1 shows the positional relationship between the *Arabidopsis thaliana* AS1 protein and decoy peptides.

The present invention is described below in detail.

The term "comprise" as used herein also includes the meanings "essentially consist of" and "consist of."

The term "gene" as used herein includes double-stranded DNA, single-stranded DNA (sense or antisense strand), and fragments thereof, unless otherwise stated. Further, the use of the term "gene" as used herein does not distinguish between regulatory region, coding region, exon, and intron, unless otherwise stated.

The terms "nucleic acid," "nucleotide," and "polynucleotide" as used herein are synonymous, and include both DNA and RNA. These may be double-stranded or single-stranded.

The decoy peptide of the present invention is a partial peptide of ASYMMETRIC LEAVES1 (AS1), and is capable of interacting with βC1 encoded by a betasatellite of a virus belonging to the family Geminiviridae.

The terms "AS1" and "βC1" as used herein mean protein, unless otherwise stated. However, when it is appropriate that the terms "AS1" and "βC1" be interpreted as gene, the terms "AS1" and "βC1" mean gene.

The decoy peptide according to the present invention means a peptide that competitively inhibit binding of a specific peptide to the original binding site in order to suppress the function of the specific peptide. Specifically, the decoy peptide according to the present invention refers to a peptide that interacts with βC1 in a plant to suppress the function of βC1, thereby suppressing a disease symptom. The phrase "capable of interacting with βC1" in the present invention can also be replaced by the phrase "capable of reducing a disease symptom caused by βC1" or the phrase "capable of improving resistance to βC1."

C1 means a pathogenicity factor encoded by a betasatellite of a geminivirus. Geminiviruses are a general term for plant viruses classified into the family Geminiviridae. The family Geminiviridae includes the genera Mastrevirus, Begomovirus, Curtovirus, and Topocuvirus. The present invention is useful especially for viruses belonging to the genus Begomovirus (in particular, monopartite type). The genus Begomovirus includes, for example, Tomato yellow leaf curl virus and Cotton leaf curl virus, both of which causes severe damage to crops. A geminivirus is often accompanied by a betasatellite. A betasatellite accompanying a geminivirus is reported to be propagated across virus species. Information about the base sequences and amino acid sequences of βC1 of viruses can easily be obtained from public databases (e.g., GenBank). When information about the base sequence and amino acid sequence of βC1 of a virus is not registered in such databases, it can be obtained by a usual method.

Examples of geminiviruses include viruses of plants of the family Malvaceae, such as Cotton leaf curl virus, Cotton chlorotic spot virus, Cotton leaf crumple virus, Cotton leaf curl Alabad virus, Cotton leaf curl Bangalore virus, Cotton leaf curl Gezira virus, Cotton leaf curl Kokhran virus, Cotton leaf curl Multan virus, Okra enation leaf curl virus, Okra leaf curl virus, Okra yellow vein virus, Okra mottle virus, Okra yellow crinkle virus, and Okra yellow mosaic virus; viruses of plants of the family Solanaceae, such as Tomato yellow leaf curl virus, Tomato leaf curl virus, Chilli leaf curl virus, Pepper golden mosaic virus, Pepper leaf curl virus, Potato yellow mosaic virus, Tomato chlorotic leaf distortion virus, Tomato chlorotic mottle virus, Tomato common mosaic virus, Tomato curly stunt virus, Tomato dwarf leaf virus, Tomato golden mosaic virus, Tomato golden mottle virus, Tomato golden vein virus, Tomato mottle virus, and Tobacco leaf curl virus; viruses of plants of the family Brassicaceae, such as Cabbage leaf curl virus; viruses of plants of the family Asteraceae, such as Ageratum yellow vein virus; viruses of plants of the family Fabaceae, such as Bean golden mosaic virus, Bean dwarf mosaic virus, Bean golden yellow mosaic virus, Soybean blistering mosaic virus, Soybean chlorotic spot virus, Soybean crinkle leaf virus, and Soybean mild mottle virus; viruses of plants of the family Gramineae, such as Maize streak virus, Sugarcane streak virus, and Wheat dwarf virus; viruses of plants of the family Euphorbiaceae, such as African cassava mosaic virus; viruses of plants of the family Convolvulaceae, such as Sweet potato leaf curl virus; viruses of plants of the family Chenopodiaceae, such as Beet curly top virus; viruses of plants of the family Caricaceae, such as Papaya leaf curl virus; viruses of plants of the family Cucurbitaceae, such as Squash leaf curl virus, Cucurbit leaf crumple virus, Pumpkin yellow mosaic virus, and Watermelon chlorotic stunt virus; and the like.

Examples of geminiviruses for which the present invention is especially effective include Tomato yellow leaf curl virus, Cotton leaf curl virus, Cotton leaf curl Multan virus, Okra enation leaf curl virus, Okra leaf curl virus, Okra yellow vein virus, Okra yellow crinkle virus, Okra mottle virus, Okra yellow mosaic virus, and Ageratum yellow vein virus.

βC1 interacts with AS1 of a host plant. The term "host plant" as used herein refers to a plant that a geminivirus infects (including both dicotyledonous plants and monocotyledonous plants). Examples of plants that are significantly damaged by infection with geminiviruses include plants of the family Solanaceae, including tomato, peppers (such as sweet pepper, green pepper, paprika, chili pepper, and other peppers), potato, petunia, and tobacco plants (such as flue-cured tobacco plants, burley tobacco plants, and like leaf tobacco plants, and *Nicotiana rustica*); plants of the family Malvaceae, including cotton, okra, kenaf, mallow, rose of Sharon, Confederate rose, hibiscus, cacao, balsa, jute, durian, Cola, and Japanese linden; plants of the family Brassicaceae, including cabbage and rapeseed; plants of the family Amaranthaceae, including beet; plants of the family Fabaceae, including common bean, soybean, and adzuki bean; plants of the family Euphorbiaceae, including cassava and jatropha; plants of the family Cucurbitaceae, including pumpkin, cucumber, and melon; plants of the family Convolvulaceae, including sweet potato; plants of the family Caricaceae, including papaya; plants of the family Gramineae, including corn, rice, sugar cane, and wheat; plants of the family Chenopodiaceae, including beet (sugar beet); and the like.

In the present invention, a plant belonging to the family Malvaceae, Solanaceae, Brassicaceae, or Fabaceae is usable as a host plant. Further, cotton, okra, kenaf, mallow, rose of Sharon, Confederate rose, hibiscus, cacao, balsa, jute, durian, Cola, Japanese linden, tomato, peppers, potato, petunia, tobacco plants, rapeseed, soybean, or common bean is usable. Among these, cotton, okra, kenaf, tomato, peppers, potato, tobacco plants, rapeseed, soybean, or common bean is particularly usable.

ASYMMETRIC LEAVES 1 (AS1) is a transcription factor having a Myb-like DNA-binding domain on the N-terminal side, and interacts with ASYMMETRIC LEAVES 2 (AS2) to regulate leaf development (NPL 1). As shown in NPL 1, the βC1 protein derived from Tomato yellow leaf curl virus also interacts with AS1 of *Arabidopsis thaliana* in addition to that of the host plant to cause disease symptoms. Additionally, as demonstrated in the Examples described later, interaction between βC1 and AS1 can be inhibited by using a partial peptide (decoy peptide) of AS1 derived from a plant other than the host plant. Thus, the decoy peptide according to the present invention does not need to be produced from AS1 derived from a host plant, and can be produced from AS1 derived from various plants. Examples of AS1 from which the decoy peptide is produced include AS1 derived from the plants mentioned above as host plants.

As an example of AS1, the base sequence of AS1 of *Arabidopsis thaliana* is registered with the website of NCBI as RefSeq Accession No. NM_129319, and the amino acid sequence of AS1 of *Arabidopsis thaliana* is registered with the website of NCBI as RefSeq Accession No. NP_181299. The base sequences of the AS1 genes of other plants can be obtained using the above sequence of *Arabidopsis thaliana* as a search query from genomic databases for crops (PlantGDB, plantgdb.org/). The base sequences of AS1 genes can also be individually obtained from a genomic database for each crop. Examples of such databases include SOL (solgenomics.net/organism/Solanum_lycopersicum/genome) for plants of the family Solanaceae, BRAD (brassicadb.org/brad/) for plants of the family Brassicaceae (rapeseed), and SoyBase (soybase.org/GlycineBlastPages/) for the family Fabaceae (soybean).

The partial peptide of AS1 according to the present invention means a peptide consisting of a portion of the amino acid sequence of AS1 or a peptide consisting of a portion of the amino acid sequence of AS1 in which any one or more amino acids are added to one or both terminals of the peptide. The number of any one or more amino acids is, for example, 1 to 50, 1 to 43, 1 to 30, 1 to 10, or 1 to 6. The length of the portion of the amino acid sequence of AS1 is, for example, 59 to 146 residues, 59 to 179 residues, 59 to 231 residues, 59 to 274 residues, or 59 to 311 residues. The length of the portion of the amino acid sequence of AS1 is, for example, 16 to 40%, 16 to 49%, 16 to 63%, 16 to 75%, or 16 to 85% of the full length of AS1, in terms of the number of amino acid residues.

The portion of the amino acid sequence of AS1 described above is not limited to portions of amino acid sequences registered in the above-mentioned databases, and broadly encompasses mutant sequences that are obtained by substituting, adding, deleting, and/or inserting one or more amino acids in such portions of the amino acid sequences, and that have biological activity similar to that before modification. Examples of mutant sequences include portions of amino acid sequences registered in the above-described databases in which one or more, for example, 1 to 50, 1 to 43, 1 to 30, 1 to 10, or 1 to 6 amino acids are substituted, added, deleted, and/or inserted.

An embodiment of the decoy peptide according to the present invention is a peptide that comprises at least one motif selected from the group consisting of (I) a leucine zipper motif, (II) a PSVTL(S/T)L motif (SEQ ID NO: 82), and (III) a coiled-coil motif, and that is capable of reducing a disease symptom caused by a virus that comprises βC1 and belongs to the family Geminiviridae. In general, the PSVTL(S/T)L motif (SEQ ID NO: 82) is an amino acid sequence found in the position near 52% of the number of the full length amino acid residues of AS1; and is found from position 195 in *Arabidopsis thaliana*, from position 187 in cotton and tomato, and from position 190 in soybean. Coiled-coil motifs of AS1 can be estimated using, for example, a prediction program (as described in Lupas et al. (1991), Predicting Coiled Coils from Protein Sequences, Science 252: 1162-1164). In *Arabidopsis thaliana* AS1, coiled-coil motifs are found in amino acids at positions 279 to 286, 298 to 305, and 327 to 334.

In the Examples described later, decoy peptides AS1d3, AS1d4, and AS1D14 were confirmed to reduce a disease symptom caused by a geminivirus. The decoy peptide AS1d3 comprises motifs (I) and (II) above, the decoy peptide AS1d4 comprises motifs (II) and (III) above, and the decoy peptide AS1D14 comprises only motif (III) above. These motifs are present not only in AS1 derived from *Arabidopsis thaliana* shown in the Examples, but also in similar sites in AS1 derived from other plants. The decoy peptide of the present invention is preferably a peptide comprising motif (III) above.

Specific examples of the "disease symptom caused by a virus that comprises βC1 and belongs to the family Geminiviridae" in the present invention include leaf curl symptoms caused by βC1.

Specific examples of the decoy peptide according to the present invention include a decoy peptide set forth in the following (A) or (B):

(A) a peptide consisting of the amino acid sequence represented by any one of SEQ ID NOs: 1 to 18, (B) a peptide consisting of the amino acid sequence represented by any one of SEQ ID NOs: 1 to 18 in which 1 to 43 amino acids are deleted, substituted, inserted, and/or added, the peptide being capable of interacting with βC1 encoded by a betasatellite of a virus belonging to the family Geminiviridae.

A specific example of the decoy peptide according to the present invention is a peptide derived from *Arabidopsis thaliana* or cotton AS1 (in a peptide that does not include the N-terminal of AS1, methionine is artificially added to its N-terminal). As demonstrated in the Examples described later, the decoy peptide (A) above has a suppression effect on the function of pathogenicity factor βC1 of geminiviruses. A person skilled in the art can obtain amino acid sequence information of a peptide having an effect similar to that of the decoy peptide (A), based on the amino acid sequence information disclosed herein. A person skilled in the art can also delete a region on the N-terminal side or the C-terminal side of the amino acid sequence of the decoy peptide (A), and obtain amino acid sequence information of a partial peptide having a similar effect. Additionally, a person skilled in the art can also modify part of the amino acids in the amino acid sequence of the decoy peptide (A), and obtain amino acid sequence information of a peptide having a similar effect.

In the peptide (B) above, the number of amino acids that are deleted, substituted, inserted, and/or added is preferably 1 to 30, more preferably 1 to 15, even more preferably 1 to 8, and particularly preferably 1 to 4. When an amino acid is substituted, substitution with an amino acid having similar properties would result in maintenance of the activity of the original peptide.

A technology for deleting, substituting, inserting, and/or adding one or more amino acids in a specific amino acid sequence is known.

It is particularly preferable to use the amino acid sequence represented by any one of SEQ ID NOs: 3, 4, 6, 7, 9, 10, and 12 to 18 in (A) and (B) above.

The decoy peptide of the present invention can be produced by, for example, a known synthesis technique such as solid phase synthesis or liquid phase synthesis, or culturing a transformant into which a nucleic acid encoding the decoy peptide is introduced. Examples of hosts for the preparation of transformants include yeasts, *Escherichia coli*, insect cells, mammalian cells, plant cells, and the like.

Purification of the produced peptide can be performed by affinity chromatography, ion-exchange chromatography, hydroxyapatite column chromatography, ammonium sulfate salting-out, or the like.

The decoy peptide of the present invention also includes salts thereof. The decoy peptide of the present invention also includes derivatives thereof. The amino acids that make up the decoy peptide of the present invention may be in the L or D form. In addition, the amino acids that make up the decoy peptide of the present invention are not limited to natural amino acids, and may be non-natural amino acids.

One kind of the decoy peptide of the present invention may be used alone, or two or more kinds of the decoy peptide of the present invention may be used in combination.

The nucleic acid of the present invention encodes the decoy peptide described above.

A person skilled in the art can convert the amino acid sequence information into base sequence information to obtain the base sequence information of the nucleic acid encoding the decoy peptide. Information on similar sequences homologous to the base sequence of the nucleic acid encoding the decoy peptide can also be obtained from public sequence databases (such as GenBank, DDBJ, and EMBL) using the BLAST program. In a nucleic acid encoding the peptide that does not include the N-terminal of AS1, a start codon may be artificially added.

Based on such base sequence information, the nucleic acid encoding the decoy peptide can be obtained by the following methods.

The kind of nucleic acid encoding the decoy peptide according to the present invention is not limited, and includes, for example, genomic DNA, cDNA, RNA, and chemically synthesized DNA and RNA. A person skilled in the art can obtain these nucleic acids by a cloning method that can generally be performed (e.g., a method disclosed in "Molecular Cloning: A Laboratory Manual (Third Edition, Sambrook and Russell, 2001, Cold Spring Harbor Laboratory Press)"). For example, a nucleic acid of interest for cloning can be extracted from a host plant of a geminivirus (plant that a geminivirus infects), and obtained by the following methods. As a method for obtaining the nucleic acid encoding the decoy peptide, a polymerase chain reaction (PCR) technology can be used. Alternatively, a nucleic acid of interest can be obtained from among the nucleic acids described above by a hybridization technology such as colony hybridization or plaque hybridization. Alternatively, a nucleic acid of interest can be obtained by combining these technologies.

The expression vector of the present invention comprises the nucleic acid described above. The expression vector is not particularly limited, and a wide variety of known expression vectors can be used. The expression vector may be an autonomously replicating vector or a vector that is incorporated into the genome of a host cell when introduced into the host cell, and that is replicated together with the chromosome(s) into which the vector has been incorporated. Methods for constructing an expression vector and introducing the expression vector into cells are well known.

The geminivirus disease control agent of the present invention comprises the aforementioned decoy peptide or the aforementioned nucleic acid encoding the decoy peptide.

The transgenic plant of the present invention is a plant transformed with the nucleic acid encoding the decoy peptide described above.

The method for reducing a disease symptom caused by a virus that comprises βC1 and belongs to the family Geminiviridae according to the present invention comprises introducing the aforementioned nucleic acid encoding the decoy peptide into a plant to transform the plant.

The geminivirus disease in the present invention means a disease caused by a geminivirus (in particular, a geminivirus comprising βC1).

Introducing the nucleic acid encoding the decoy peptide into a plant to express the decoy peptide in the plant, introducing the decoy peptide into a plant, or applying to a plant the control agent comprising the decoy peptide or the nucleic acid encoding the decoy peptide enables control of the geminivirus disease or reduction in a disease symptom caused by a virus that comprises βC1 and belongs to the family Geminiviridae.

The nucleic acid is introduced into a plant in such a manner that the decoy peptide encoded by the nucleic acid is expressed. The term "in such a manner that the decoy peptide encoded by the nucleic acid is expressed" generally means a state in which transcription and translation of mRNA derived from the nucleic acid is performed. Thus, a promoter and a terminator effective for expression, and other transcription and translation regulatory sequences are also generally introduced into a plant simultaneously. The introduction into a plant means that the nucleic acid is introduced as a genetic material into a plant.

Examples of the method for introducing the nucleic acid into a plant include a physical method using a reagent for nucleic acid introduction and a particle gun (gene gun) or using a nucleic acid agrochemical, and a biological method using *Agrobacterium* or virus. The duration of the effect of the introduction of the genetic material may be transient, or permanent, i.e., the genetic material may continue to be inherited by the progeny. Either a method that provides a transient effect or a method that provides a permanent effect may be used.

Examples of the method that provides a transient effect of the genetic material include a method using a nucleic acid agrochemical wherein RNA or DNA is sprayed on a plant. Bacteria or viruses, such as *Agrobacterium* or viruses, for introducing the nucleic acid into a host are also usable. Examples of usable *Agrobacterium* include LBA4404 strain, EHA101 strain, GV3101 strain, etc., which lack pathogenicity for plants. Viral vectors that show no pathogenicity for plants are also usable. Examples include Cucumovirus, Potexvirus, Potyvirus, Tobamovirus, Begomovirus, and the like.

Examples of the method that provide a permanent effect such that the genetic material continues to be inherited by the progeny of a plant include a method in which the genetic material is incorporated into a chromosome of a plant cell, a method in which an artificial chromosome is constructed extrachromosomally in a plant and the genetic material is incorporated into the artificial chromosome and maintained, and other methods.

According to the decoy peptide of the present invention, the expression can continue in the progeny of a plant into which the genetic material is introduced, as described above. The present invention is thus also useful for the production of seeds and seedlings of plants expressing the decoy peptide. That is, methods for producing and using, for example, pollen and like reproductive materials, cut flowers, cells capable of tissue culture, and cells and seeds capable of regeneration into plants, of plants comprising the nucleic acid encoding the decoy peptide, are also embodiments of the present invention.

Transformation with the nucleic acid includes the case in which the nucleic acid is exogenously introduced to perform transformation, and the case in which endogenous AS1 homologous gene on a chromosome of a plant itself is modified to express the decoy peptide shown in the present invention. For example, a genome-editing technology using a DNA-cleaving (or modifying) enzyme with a specific base sequence recognition domain, such as CRISPR/Cas9, TALEN, or ZFN, can be used. The genome of a plant can be modified such that the decoy peptide is expressed from the endogenous AS1 homologous gene of the plant, by editing the positions of the start codon and the stop codon in such a manner that part of the endogenous AS1 gene is deleted.

The decoy peptide of the present invention can be expressed from the nucleic acid, and it is also possible to exogenously introduce the decoy peptide itself into a plant. For example, an embodiment using a peptide agrochemical, i.e., an embodiment in which the decoy peptide is sprayed together with a peptide introduction reagent, is also possible.

Examples of plants to which the control agent of the present invention is applied and plants that are transformed include host plants of geminiviruses, i.e., plants that geminiviruses infect. Specific examples include the host plants described above.

The geminivirus disease control agent of the present invention may be formulated together with agrochemical adjuvants into various forms, such as emulsifiable concentrates, suspension concentrates, dusts, granules, wettable powders, water soluble powders, soluble concentrates, flowables, water dispersible granules, aerosols, pastes, and ultra-low-volume formulations, in the same manner as in conventional agrochemical formulations. When such formulations are actually used, they may be used unmodified, or after being diluted with diluents such as water to a predetermined concentration. Examples of agrochemical adjuvants include carriers, emulsifiers, suspending agents, dispersants, spreaders, penetrating agents, wetting agents, thickeners, stabilizers, and the like.

The geminivirus disease control agent of the present invention may also be formulated into various forms, using reagents for introducing a nucleic acid or a peptide, such as nanoparticles (liposomes, amphiphilic lipid membranes, and peptides), carborundum, and polyethylene glycol. Such a geminivirus disease control agent of the present invention may also be formulated together with the conventional agrochemical formulations described above. When such formulations are actually used, they may be used unmodified or after being diluted with diluents such as water to a predetermined concentration.

The geminivirus disease control agent of the present invention may be applied by a common method for application that is generally performed, such as spraying (e.g., spraying, spreading, misting, atomizing, grain diffusing, or application on water surface), soil application (e.g., mixing or drenching), surface application (e.g., coating, powdering, or covering), or impregnation to obtain poisonous feed. The geminivirus disease control agent of the present invention may also be applied by a so-called ultra-low-volume application method.

The use of the decoy peptide of the present invention makes it possible to suppress disease symptoms caused by pathogenicity factor βC1 expressed by geminiviruses in host plants. Moreover, problems are relatively less likely to be caused in the method using the decoy peptide of the present invention than in conventional technologies, in terms of the effect persistence when a mutant viral strain appears, safety, cost, etc.

The method for evaluating the degree of reduction in a disease symptom caused by a virus that comprises βC1 and belongs to the family Geminiviridae according to the present invention comprises simultaneously introducing βC1 encoded by a betasatellite of a virus belonging to the family Geminiviridae and a decoy peptide capable of interacting with the βC1 into a plant such that the βC1 and the decoy peptide are transiently expressed.

The βC1 and the decoy peptide may be transiently expressed in a plant by the methods described above. Examples of plants to which the method of the present invention can apply include host plants of geminiviruses, i.e., plants that geminiviruses infect. Specific examples include the host plants described above. In this method, the geminivirus, βC1, decoy peptide, and the like are the same as described above. Examples of disease symptoms caused by geminiviruses comprising βC1 include leaf curl symptoms caused by βC1.

When the βC1 and the decoy peptide are introduced such that they are transiently expressed, they are preferably introduced into the same place of a plant. The term "simultaneously" does not need to mean simultaneous in a strict sense, and an introduction time difference of about several hours is also allowed. In the method of evaluation, the degree of reduction in the disease symptom can be determined, for example, by comparing with a control into which the decoy peptide to be transiently expressed is not introduced.

Conventional methods, which involve preparation of a transgenic plant, require about 1 to 2 years for evaluation, whereas the method of evaluation of the present invention enables evaluation in about 2 to 4 months, including the period for growing a plant. The method of evaluation of the present invention thus enables the degree of reduction, in a disease symptom caused by a geminivirus, due to the decoy peptide to be evaluated in a far shorter period of time than the conventional methods.

Additionally, with the conventional methods, which involve preparation of a transgenic plant, the decoy peptide is basically expressed throughout the plant; therefore, if the pathogenicity factor of a geminivirus moves, since the disease symptom is also reduced in the place to which the pathogenicity factor moves, it is difficult to evaluate the movement suppression effect. According to the method of evaluation of the present invention, however, since the decoy peptide is transiently expressed in only a specific place of a plant, when the pathogenicity factor of a geminivirus moves, a disease symptom appears in the place to which the pathogenicity factor moves; therefore, the movement suppression effect due to the decoy peptide can be evaluated.

EXAMPLES

The present invention is described in more detail below with reference to Examples. These examples are given to illustrate specific embodiments of the present invention, and should not be construed in any sense as limiting or restricting the scope of the invention disclosed herein. It should be understood in the present invention that various embodiments can be made or executed within the spirit, scope, and concept disclosed herein.

Methods for general biochemical experiments and molecular biology experiments, such as purification and electrophoresis of a protein, cleavage and ligation of DNA, bacterial transformation, determination of the base sequence of a gene, and PCR, were basically carried out according to a manual attached to a commercially available reagent, equipment, etc., for use in each operation and an experimental manual (e.g., "Molecular Cloning: A Laboratory Manual (Third Edition, Sambrook and Russell, 2001, Cold Spring Harbor Laboratory Press)"). For PCR reaction, GeneAmp (trademark) PCR system 9700 (Applied Biosystems) was used. Each apparatus was operated, unless otherwise disclosed herein specifically, by a standard operation procedure described in a manual attached to the apparatus. All of the examples were carried out or can be carried out, unless otherwise disclosed herein specifically, by standard technologies that are well known and conventional to those skilled in the art.

Plant Cultivation

The *Nicotiana benthamiana* used in the experiments was cultivated at 23° C. under conditions of a 16-hour light period and an 8-hour dark period.

Cloning of AS1 Genes, Decoy Peptide Genes, and βC1 Genes

The DNA of each of various kinds of genes was subjected to PCR using the following primers and Easy-A High-Fidelity PCR Cloning Enzyme (Stratagene), and then cloned into pCR8 (Thermo Fisher Scientific). The DNA used as a template for PCR was prepared as follows. For each AS1 gene, the total RNA of the plant below from which the gene was derived was extracted using a NucleoSpin RNA Plant kit (Takara Bio Inc.), and 1st strand cDNA was reverse-transcribed using a PrimeScript RT reagent kit (Takara Bio Inc.). For each βC1 gene, the ORF was cloned using the GeneArt artificial gene synthesis service of Thermo Fisher Scientific, and used as template DNA. For the following 20 kinds of decoy genes as candidates for decoy peptides, the cDNA of the *Arabidopsis thaliana* or cotton AS1 gene was used as a template.

AS1

Cotton AS1 gene GaAS1 (origin: *Gossypium arboreum*, cultivar name: Dwarf cotton (tree cotton), product of Sakata Seed Corporation)

```
                              (SEQ ID NO: 19)
ACCATGAAGGAGAGACAGCGGTGGAG

                              (SEQ ID NO: 20)
TCACTGCCCATTAGGCTCCACAAC
```

Tomato AS1 gene SlAS1 (origin: *Solanum lycopersicum*, cultivar name: Micro Tom)

```
                              (SEQ ID NO: 21)
ACCATGAGGGAGAGGCAACGGTGGCGA

                              (SEQ ID NO: 22)
TTAGCGGCCACCATTAGGTTCTGCAAGTC
```

*Arabidopsis thaliana* AS1 gene (origin: *Arabidopsis thaliana* Col-0 strain)

(SEQ ID NO: 23)
ACCATGAAAGAGAGACAACGTTGGAG (SEQ ID NO: 24)
TCAGGGGCCGTCTAATCTGC

Soybean AS1 gene GmAS1 (origin: *Glycine max*, cultivar name: Enrei)

(SEQ ID NO: 25)
ACCATGAAAGATAGGCAACGTTGGAG (SEQ ID NO: 26)
CTATCTTCCATTTGGTTCAGTGAG

Decoy Peptides Derived from *Arabidopsis thaliana* AS1

AS1 d1
(SEQ ID NO: 27)
ACCATGAAAGAGAGACAACGTTGGAG (SEQ ID NO: 28)
TCAGACAACGTTAGACCGCTCTTT

AS1 d2
(SEQ ID NO: 29)
ACCATGAAAGAGAGACAACGTTGGAG (SEQ ID NO: 30)
TCAAGGCGCGATCACTGGGTTA

AS1 d3
(SEQ ID NO: 31)
ACCATGAAGCAACAGAGAGAAGAGAAAGAGAG (SEQ ID NO: 32)
TCAGAACACACTCTCGCTACTC

AS1 d4
(SEQ ID NO: 33)
ACCATGTGGTTAGCTACTTCTAACAATGGGAAC (SEQ ID NO: 34)
TCAGGGGCGGTCTAATCTGC

AS1 d5
(SEQ ID NO: 35)
ACCATGAAGAAAGGGTCTTTGACAGAG (SEQ ID NO: 36)
TCATCTTAGCCTCCATGCAGCCTCTTTC

AS1 d6
(SEQ ID NO: 37)
ACCATGAAGAAAGGGTCTTTGACAGAG (SEQ ID NO: 38)
TCATCTGTACTCTCCTTCGATCTTC

AS1 d7
(SEQ ID NO: 39)
ACCATGAAGAAAGGGTCTTTGACAGAG (SEQ ID NO: 40)
TCAGGGGCGGTCTAATCTGC

AS1 d8
(SEQ ID NO: 41)
ACCATGCGGTTAGGGAAGTGGTGGGAAG (SEQ ID NO: 42)
TCATCTTAGCCTCCATGCAGCCTCTTTC

-continued

AS1 d9
(SEQ ID NO: 43)
ACCATGCGGTTAGGGAAGTGGTGGGAAG (SEQ ID NO: 44)
TCATCTGTACTCTCCTTCGATCTTC

AS1 d10
(SEQ ID NO: 45)
ACCATGCGGTTAGGGAAGTGGTGGGAAG (SEQ ID NO: 46)
TCAGGGGCGGTCTAATCTGC

AS1 d11
(SEQ ID NO: 47)
ACCATGGCTAATTCGAATGGAGGGTTT (SEQ ID NO: 48)
TCAGGGGCGGTCTAATCTGC

AS1 D12
(SEQ ID NO: 49)
ACCATGGTTGTTGCAAGGCCTCCCTC (SEQ ID NO: 50)
TCAGGGGCGGTCTAATCTGC

AS1 D13
(SEQ ID NO: 51)
ACCATGTCGGTAACTTTGACATTATCG (SEQ ID NO: 52)
TCAGGGGCGGTCTAATCTGC

AS1 D14
(SEQ ID NO: 53)
ACCATGGCTTGGGCAGACCATAAG (SEQ ID NO: 54)
TCAGGGGCGGTCTAATCTGC

Decoy Peptides Derived from Cotton AS1

GaAS1 D1
(SEQ ID NO: 55)
ACCATGTGGCTTTCTAATTCCAGCAATGCATCC (SEQ ID NO: 56)
AGGCTCCACAACCCTGGGTC

GaAS1 D2
(SEQ ID NO: 57)
ACCATGGTCACACCACCTTCCCCTTC (SEQ ID NO: 58)
AGGCTCCACAACCCTGGGTC

GaAS1 D3
(SEQ ID NO: 59)
ACCATGTCTGTGACTTTAAGCTTATCTCCCTCAAC (SEQ ID NO: 60)
AGGCTCCACAACCCTGGGTC

GaAS1 D4
(SEQ ID NO: 61)
ACCATGGCTTGGGTTGCACATAGAAAGGAAG (SEQ ID NO: 62)
AGGCTCCACAACCCTGGGTC

GaAS1 D1ngq
(SEQ ID NO: 63)
ACCATGTGGCTTTCTAATTCCAGCAATGCATCC (SEQ ID NO: 64)
TCACTGCCCATTAGGCTCCACAAC -continued GaAS1 D4ngq (SEQ ID NO: 65)
ACCATGGCTTGGGTTGCACATAGAAAGGAAG (SEQ ID NO: 66)
TCACTGCCCATTAGGCTCCACAAC

βC1

βC1-TYLCCNB (origin: Tomato yellow leaf curl China virus-associated DNA beta, isolate Y10, GenBank accession No. AJ781300)

(SEQ ID NO: 67)
ACCATGACTATCAAATACAACAACATG (SEQ ID NO: 68)
TCATACATCTGAATTTGTAAATACATC

βC1-CLCuMB (origin: Cotton leaf curl virus-associated DNA beta, GenBank accession No. FN554719)

(SEQ ID NO: 69)
ACCATGACAACGAGCGGAAC (SEQ ID NO: 70)
TTAAACGGTGAACTTTTTATTGAATACG

Test Example 1

Experiments for Interaction Between AS1 and βC1 and Experiments

For Inhibition of Interaction by Decoy Peptide Preparation of AS1, Decoy Peptides, and βC1

For various kinds of AS1 proteins and decoy peptide candidate proteins, recombinant proteins were purified as follows. The cDNA of each of the proteins was subcloned into the 3'-terminal region of the maltose-binding protein (MBP) gene of pMAL-c2× (NEB), which is a maltose-binding protein fusion expression vector. A list of the cDNAs is shown below. The obtained plasmid DNAs were introduced into Rosetta (DE3) (Novagen) and routinely cultured to an absorbance (600 nm) of 0.8, and recombinant protein expression was induced by culture with shaking at 16° C. and addition of IPTG (final concentration: 1 mM). The MBP-fused proteins were affinity-purified using MBP-Trap HP (GE). The collected protein solutions were concentrated with a 30K NMWL Amicon Ultra-4 centrifugal filter unit (Merck Millipore). The peptides indicated as AS1d3, AS1d5, and AS1d8 were degraded in a strain of *Escherichia coli*, and thus could not be isolated and purified (data not shown).

MBP-Fused Proteins

Cotton AS1 gene GaAS1 (origin: *Gossypium arboreum*)

Tomato AS1 gene SlAS1 (origin: *Solanum lycopersicum*)

*Arabidopsis thaliana* AS1 gene (origin: *Arabidopsis thaliana*) Position (corresponding amino acid position in *Arabidopsis thaliana* AS1 (FIG. 1))

AS1 1-367 (SEQ ID NO: 71)
AS1 d1 1-145 (SEQ ID NO: 1)
AS1 d2 1-179 (SEQ ID NO: 2)
AS1 d3 Met-106-250 (SEQ ID NO: 3)
AS1 d4 Met-180-367 (SEQ ID NO: 4)
AS1 d5 Met-58-280 (SEQ ID NO: 5)
AS1 d6 Met-58-324 (SEQ ID NO: 6)
AS1 d7 Met-58-367 (SEQ ID NO: 7)
AS1 d8 Met-95-280 (SEQ ID NO: 8)
AS1 d9 Met-95-324 (SEQ ID NO: 9)
AS1 d10 Met-95-367 (SEQ ID NO: 10)
AS1 d11 Met-156-367 (SEQ ID NO: 11)

For various kinds of C proteins, recombinant proteins were purified as follows. The cDNA of each of the proteins was subcloned into the 3'-terminal region of the glutathione S-transferase (GST) gene of pGEX-2TK (GE). A list of the cDNAs is shown below. The obtained plasmid DNAs were introduced into Rosetta (DE3) (Novagen) and routinely cultured to an absorbance (600 nm) of 0.8, and recombinant protein expression was induced by culture with shaking at 16° C. and addition of IPTG (final concentration: 1 mM). The GST-fused proteins were affinity-purified using GSTrap HP (GE). The collected protein solutions were subjected to concentration and replacement of the buffer with DA buffer (20 mM Tris-HCl at pH 7.4/200 mM NaCl/10 mM thioglycerol/10% glycerol), using a 30K NMWL Amicon Ultra-4 centrifugal filter unit.

GST-Fused Proteins

βC1-TYLCCNB (origin: Tomato yellow leaf curl China virus-associated DNA beta, isolate Y10)

βC1-CLCuMB (origin: Cotton leaf curl virus-associated DNA beta)

In Vitro, Pulldown and Competitive Pulldown, Assays

Experiments for interaction between GST-fused βC1 and MBP-fused AS1 were performed as follows. 2 μg of GST-fused βC1 and an equal amount of MBP-fused AS1 were mixed in pulldown buffer (50 mM Tris-HCl at pH 7.5/100 mM NaCl/0.25% Triton X-100/35 mM thioglycerol) at room temperature for 2 hours. At this time, the supernatant was sampled as input proteins, an equal amount of 2×SDS-PAGE sample buffer was added, and the mixture was freeze-preserved as an input sample. Subsequently, 25 μL of Glutathione Sepharose HP beads (GE) was added, followed by shaking at room temperature for 1 hour. Centrifugation was performed with a small-sized centrifuge at about 5,000 rpm for 30 seconds, the beads were washed with pulldown buffer six times, 25 μL of 2×SDS-PAGE sample buffer was added, and the mixture was freeze-preserved as a pulldown sample.

To detect AS1 that interacted with βC1, proteins co-precipitated with the beads were subjected to SDS-PAGE (6% acrylamide gel), and immunoblotting was performed using an anti-MBP monoclonal antibody (HRP conjugated, NEB) and Amersham ECL Prime (GE). To confirm that these kinds of proteins had been used in equal amounts, the same membrane was regenerated, and immunoblotting was also performed using an anti-GST-tag polyclonal antibody (MBL). Further, for detection of the input sample, immunoblotting was performed in a manner similar to that for the samples co-precipitated with the beads.

Figure 2:
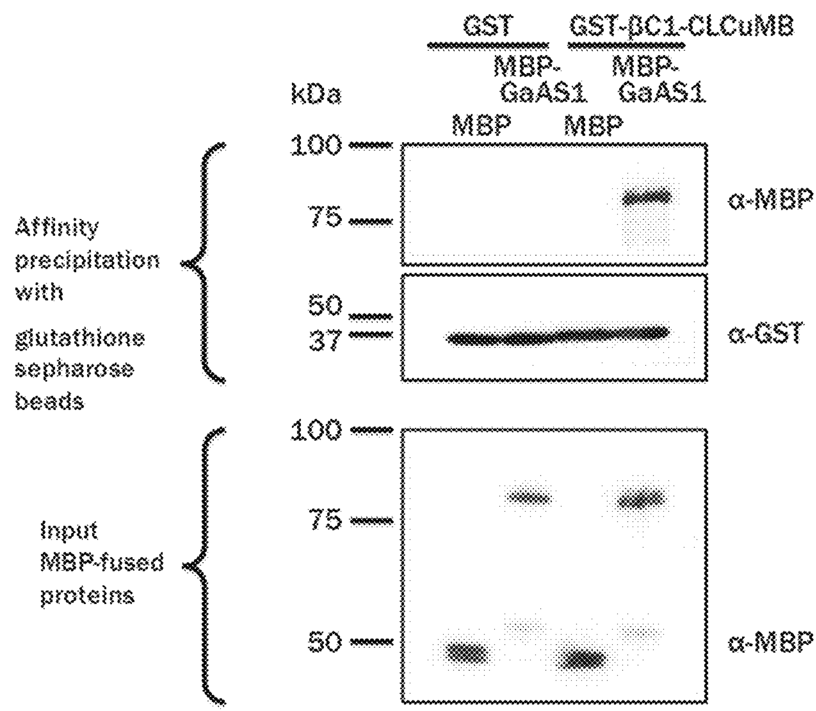
FIG. 2 shows pictures indicating the results of an experiment for interaction between the cotton AS1 protein (GaAS1) and the βC1 protein derived from Cotton leaf curl virus (βC1-CLCuMB). Samples co-precipitated with beads to be bound to GST were detected with an anti-MBP antibody (top) and an anti-GST antibody (middle). The bottom picture shows detection of the input proteins with an anti-MBP antibody. The top picture shows interaction between the βC1 protein and the AS1 protein. The bottom two pictures Show that these kinds of proteins were added in equal amounts.
Figure 3:
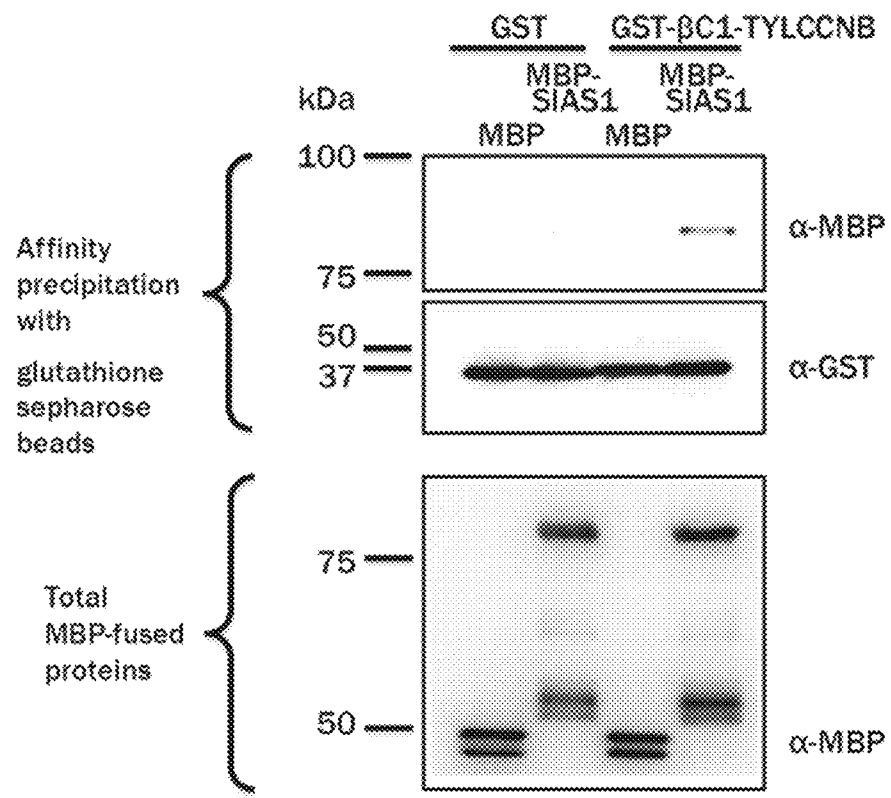
FIG. 3 shows pictures indicating the results of an experiment for interaction between the tomato AS1 protein (S1AS1) and the βC1 protein derived from Tomato yellow leaf curl virus (βC1-TYLCCNB). Samples co-precipitated with beads to be bound to GST were detected with an anti-MBP antibody (top) and an anti-GST antibody (middle). The bottom picture shows detection of the input proteins with an anti-MBP antibody. The top picture shows interaction between the βC1 protein and the AS1 protein. The bottom two pictures show that these kinds of proteins were added in equal amounts.

FIG. 2 shows the results of the pulldown assay using the GST-fused βC1 protein derived from Cotton leaf curl virus and the MBP-fused cotton AS1 protein. FIG. 3 shows the results of the pulldown assay using the GST-fused βC1 protein derived from Tomato yellow leaf curl virus and the MBP-fused tomato AS1 protein. The results of the in vitro pulldown assays in FIGS. 2 and 3 reveal that both interaction between the cotton AS1 protein (GaAS1) and the βC1 protein derived from Cotton leaf curl virus (βC1-CLCuMB), and interaction between the tomato AS1 protein (SlAS1) and the βC1 protein derived from Tomato yellow leaf curl virus (βC1-TYLCCNB) were detected. From these results, βC1 is also believed to be a pathogenicity determinant of a leaf curl symptom in tomato and cotton.

Experiments for inhibition of interaction using GST-fused βC1, MBP-fused AS1, and decoy peptides (AS1d1, AS1d2, and AS1d4) were performed in the same manner as in the experiments for interaction above, except for the following. After GST-fused βC1 and varying amounts of a MBP-fused decoy peptide were mixed in pulldown buffer at room temperature for 1 hour, MBP-fused AS1 in an amount equal to that of the GST-fused βC1 was added, and the mixture was further mixed at room temperature for 1 hour. At this time, 25 μL of the supernatant was sampled as input proteins. Subsequently, 25 μL of Glutathione Sepharose HP beads was added, followed by shaking at room temperature for 1 hour. The beads were then washed with pulldown buffer six times, and a pulldown sample was freeze-preserved.

Figure 4:
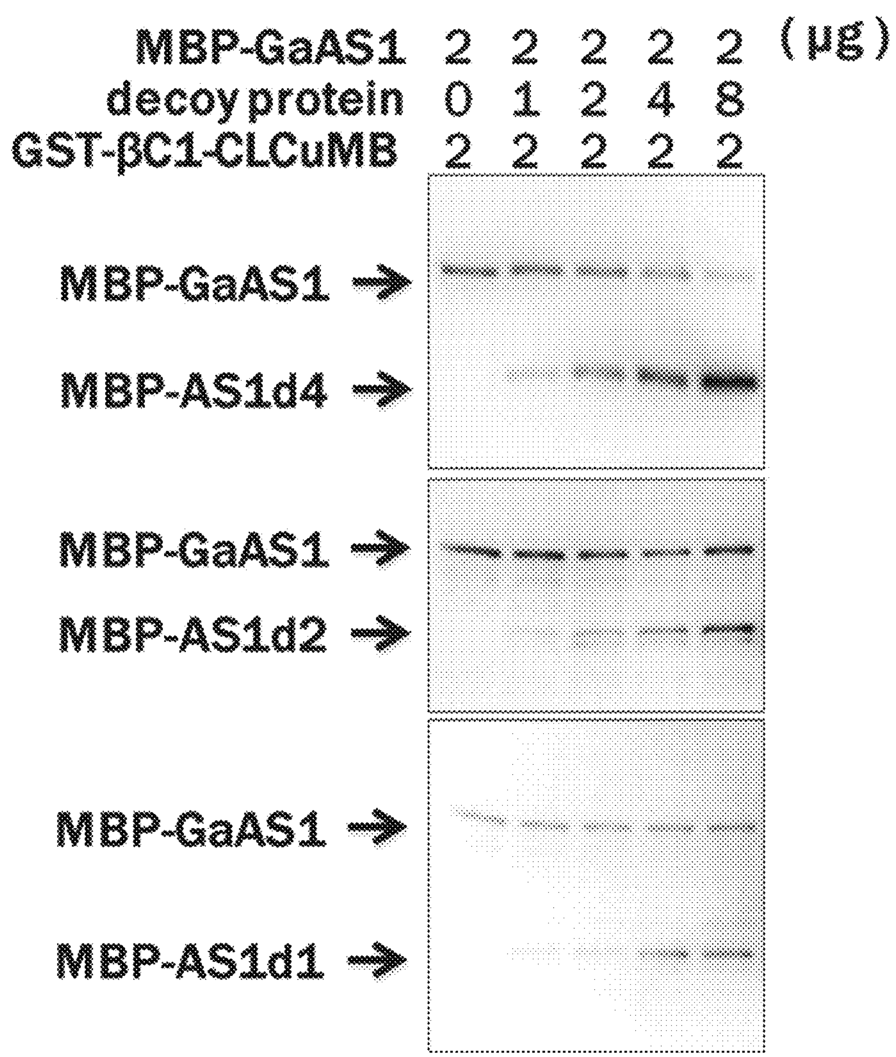
FIG. 4 shows pictures indicating the results of experiments for inhibition of interaction between the cotton AS1 protein and the βC1 protein derived from Cotton leaf curl virus, using decoy peptides. The decoy peptides used are AS1d4, AS1d2, and AS1d1 in order from the top. Samples co-precipitated with beads to be bound to GST were detected with an anti-MBP antibody.
Figure 5:
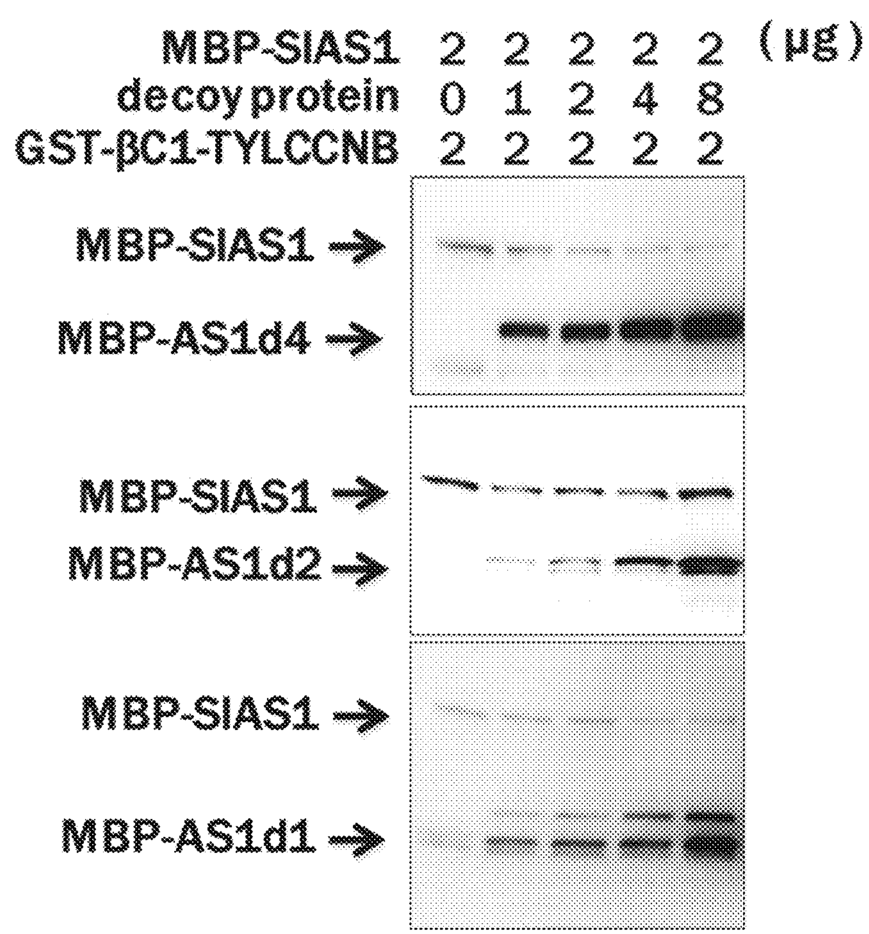
FIG. 5 shows pictures indicating the results of experiments for inhibition of interaction between the tomato AS1 protein and the βC1 protein derived from Tomato yellow leaf curl virus, using decoy peptides. The decoy peptides used are AS1d4, AS1d2, and AS1d1 in order from the top. Samples co-precipitated with beads to be bound to GST were detected with an anti-MBP antibody.

FIG. 4 shows the results of the experiment using the GST-fused βC1 protein derived from Cotton leaf curl virus and the MBP-fused cotton AS1 protein. FIG. 5 shows the results of the experiment using the GST-fused βC1 protein derived from Tomato yellow leaf curl virus and the MBP-fused tomato AS1 protein. The results of the in vitro experiments for inhibition of interaction shown in FIGS. 4 and 5 revealed that when d4 was added, inhibition of interaction between cotton AS1 (GaAS1) and βC1-CLCuMB was detected in a concentration-dependent manner, and that inhibition of interaction by d4 was also detected in the experiment using tomato AS1 (SlAS1) and βC1-TYLCCNB. From these results, the decoy peptide is believed to function effectively as a technology for suppressing βC1.

Figure 6:
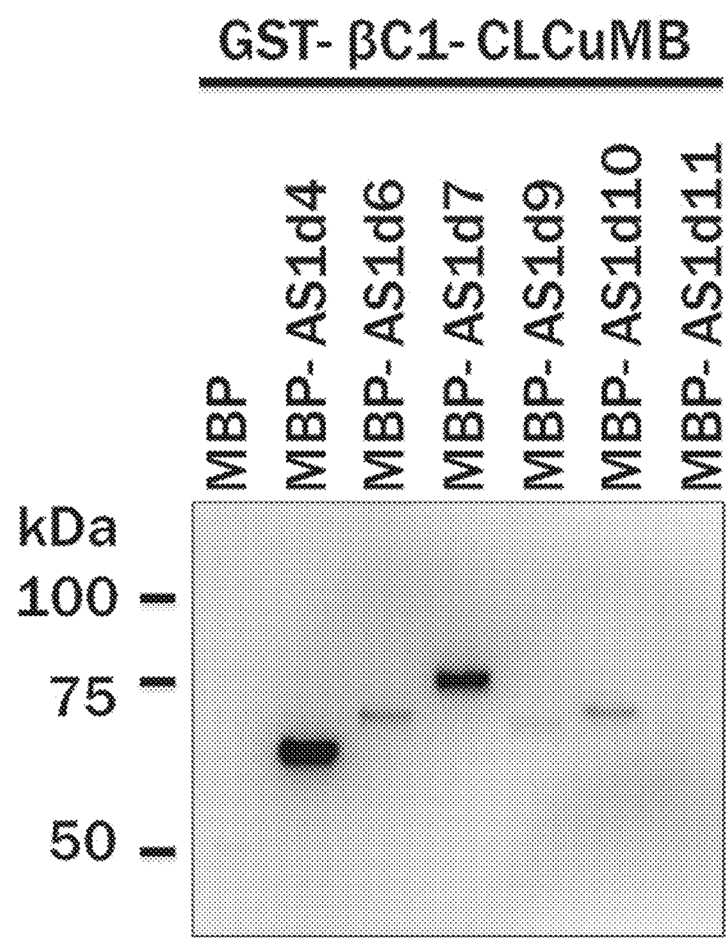
FIG. 6 shows a picture showing the results of experiments for interaction between decoy peptides (AS1d4, AS1d6, AS1d7, AS1d9, AS1d10, and AS1d11) and the βC1 protein derived from Cotton leaf curl virus.

In the same manner as in the experiments for interaction between GST-fused βC1 and MBP-fused AS1, interaction between the βC1 protein derived from Cotton leaf curl virus and the other decoy peptides (AS1d4, AS1d6, AS1d7, AS1d9, AS1d10, AS1d11) was also investigated. FIG. 6 shows the results.

Test Example 2

Experiment for Confirming Effect of Decoy Peptides in Plant

Generation of Genetically Modified Plants Using Decoy Peptide Genes

To investigate the effect of a decoy peptide in a plant, an experiment for genetic modification of *Nicotiana benthamiana*, which is a plant of the family Solanaceae, was performed. The DNA constructs used for the experiment for genetic modification were constructed on Bin19-based binary vectors. For decoy peptides, each of four kinds of partial sequences of *Arabidopsis thaliana* AS1 gene (AS1d1, AS1d2, AS1d3, and AS1d4) was subcloned such that it was controlled by a CaMV35S promoter and a NOS terminator. In a control experiment, the *Arabidopsis thaliana* AS1 gene or the GFP gene was used instead of the decoy peptide genes.

Generation of genetically modified plants was performed according to the method of Matsumoto et al. (Cell Technology, 1989, Vol. 8, p. 721-727) to obtain genetically modified plants (T1 generation). From these, plants in which the transgene was a single copy were selected. Their seeds were collected, and progeny plants (T2 generation) were generated. From these, homozygous plants were selected, and their seeds (T3 generation) were collected. For the experiment described below, the seeds (T3 generation, homozygote) collected from the T2 plants were used.

Quantification of Expression of Transgene

In T3 plants obtained by sowing the seeds above, the expression level of the transgene was investigated. The total RNA was extracted from a seedling plant cultivated for two weeks in sterile medium, and relative quantification was performed by the comparative CT method of real-time RT-PCR (ABI PRISM 7700 Sequence Detection System User Bulletin #2: Relative Quantification of Gene Expression). For the total RNA extraction and reverse transcription reaction, a NucleoSpin RNA Plant PrimeScript RT reagent kit (Takara Bio Inc.) was used. For real-time PCR measurement, Power SYBR Green PCR Master Mix (Thermo Fisher Scientific) was used. As PCR primers, a combination of CCGAGAGAATGGCATCTTTG (SEQ ID NO: 72) and AGACCCTTTCTTGATCCCTGG (SEQ ID NO: 73) for the full length of AS1, AS1d1, and AS1d2; and a combination of TTATCGCCTTCCACAGTGGCT (SEQ ID NO: 74) and TCCCACTACAAGACGGCATCA (SEQ ID NO: 75) for AS1d3 and AS1d4 were used. As an internal standard, actin gene was detected with a combination of AGCCACACCGTCCCAATTTA (SEQ ID NO: 76) and CACGCTCGGTAAGGATCTTCA (SEQ ID NO: 77).

Seeds of a line having a high level of transcription of the transgene among the T3 plants obtained using each DNA construct to be introduced were used in the experiment described below.

Assessment of Disease Symptom Caused by βC1 in *Nicotiana benthamiana* Plant

Resistance to βC1 in genetically modified plants was evaluated by expressing βC1 transiently by injection of *Agrobacterium* in the plants. The DNA construct used for this experiment was constructed on a Bin19-based binary vector. The βC1 gene derived from Tomato yellow leaf curl virus used in the above experiments for interaction and for inhibition of interaction was subcloned such that it was controlled by a CaMV35S promoter and a NOS terminator, and transformation of *Agrobacterium* strain EHA101 was performed. For a control group, *Agrobacterium* having T-DNA that expresses GFP gene with p35S was prepared.

These Agrobacteria were cultured with shaking in LB medium supplemented with a selection antibiotic (hygromycin: 100 mg/L) at 30° C. for 24 hours. The cells were collected at 3,000 rpm for 15 minutes with a Hitachi tabletop centrifuge, and inoculums were prepared using an infiltration buffer (1 mM MES pH 5.6, 1 mM $MgCl_2$, 100 μM Acetosyringone). Each inoculum was injected using a 1 mL-syringe into an area that was 70% or more of two upper expanded leaves of *Nicotiana benthamiana* cultivated for one month. The total amount of injection into the genetically modified plants generated using each transgene was 5 mL per 40 leaves of 20 plants.

As a result, a leaf curl symptom appeared from the second upper leaf from the inoculated leaves. Thus, from 11 days after the inoculation, the symptom scores of the leaf curl symptom that appeared on the second and third upper leaves were recorded. What percentage of the outer circumference whose outer peripheral edge portion was curled in each of the two leaves per plant was investigated, and rated on a scale of 0 to 100. The average value of the scores in a plant was regarded as the symptom score of the plant (see the rightmost pictures of FIG. 7). The symptom scores of 20 plants were recorded for each transgene, and the average value of the scores was calculated. In a statistical test for the average values, multiple comparisons using Dunnett's method were performed with software R version 3.1.0 (r-project.org/).

Figure 7:
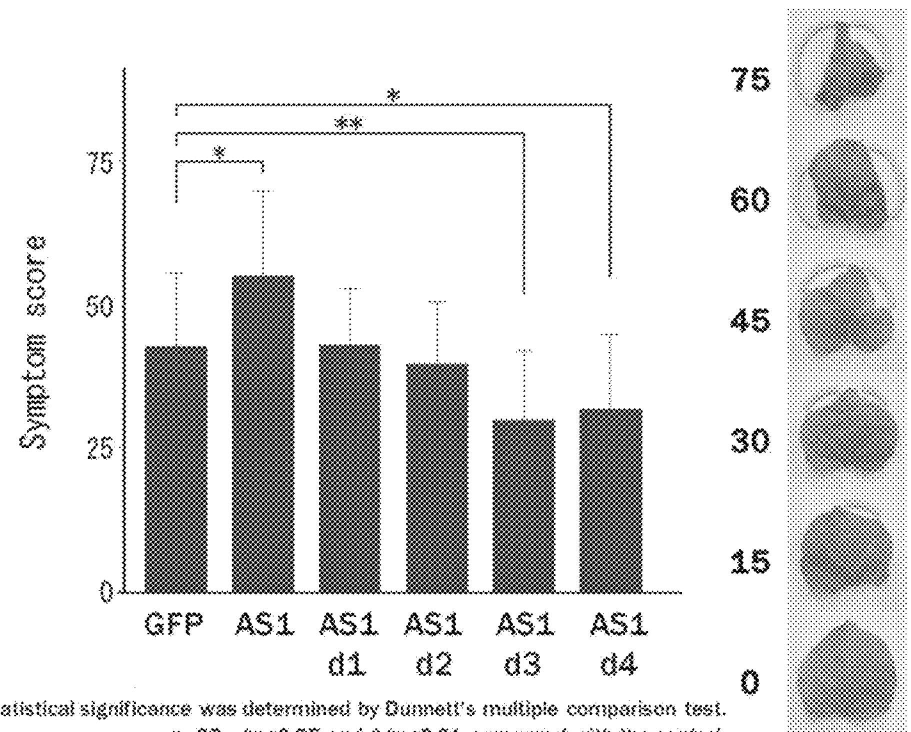
FIG. 7 (left) is a graph indicating the score of a disease symptom (symptom score) caused by βC1 in a genetically modified plant (*Nicotiana benthamiana*) that expresses GFP, AS1, or a decoy peptide. Black bars indicate the average values in experimental groups, and error bars are standard deviations. The statistical significance was determined by multiple comparisons using Dunnett's method (n=20.

FIG. 7 shows the results. The results of FIG. 7 revealed that the leaf curl symptom caused by βC1 was suppressed in the genetically modified plants into which the decoy peptide d3 gene or the decoy peptide d4 gene was introduced, whereas the disease symptom caused by βC1 was worsened in the genetically modified plants into which *Arabidopsis thaliana* AS1 gene was introduced. These results indicate that using a partial peptide of AS1, rather than the full length of AS1, is effective for suppressing the disease symptom caused by βC1.

Test Example 3

Short-Term Method for Evaluating Suppression Effect on Disease Symptom Caused by βC1 and Suppression Effect on Movement of βC1 in Plant An experiment was performed to investigate whether the disease symptom caused by βC1 transiently expressed in the plants shown in Test Example 2 can be suppressed by another gene simultaneously co-introduced. The DNA constructs used in this experiment can be the same as those shown in Test Example 2. Specifically, they are genes constructed on binary vectors such as Bin19-based binary vectors and subcloned such that expression in plant cells was controlled by, for example, a CaMV35S-derived promoter and a NOS terminator. The βC1 gene used was derived from Tomato yellow leaf curl virus. The gene co-introduced was the gene of decoy peptide d4.

*Agrobacterium* transformation was performed using these DNA constructs. The resulting Agrobacteria were cultured with shaking in LB medium supplemented with a selection antibiotic at 30° C. for 24 hours. The cells were collected at 3,000 rpm for 15 minutes with a Hitachi tabletop centrifuge, and resuspended with infiltration buffer (1 mM MES pH 5.6, 1 mM $MgCl_2$, 100 μM Acetosyringone). After adjusting the absorbance (600 nm) to 1.0, the suspension containing the βC1 gene and the suspension containing the decoy peptide gene to be co-introduced were mixed in a ratio of the suspension containing the βC1 gene:the suspension containing the decoy peptide gene to be co-introduced=1:9. For comparison with the decoy peptide gene to be co-introduced, an *Agrobacterium* mixture containing vector DNA (pBI101) was prepared, and the suspension containing the βC1 gene and the suspension containing the vector were mixed in a ratio of the suspension containing the βC1 gene:the suspension containing the vector=1:9. Each inoculum was injected using a 1 mL-syringe into an area that was 70% or more of two upper expanded leaves of *Nicotiana benthamiana* cultivated for one month.

From 12 days after the inoculation, the symptom scores of the leaf curl symptom that appeared on the second and third upper leaves from the inoculated leaves were recorded. What percentage of the outer circumference whose outer peripheral edge portion was curled in each of the two leaves per plant was investigated, and rated on a scale of 0 to 100. The average value of the scores in a plant was regarded as the symptom score of the plant. A Wilcoxon rank sum test was performed with software R version 3.1.0.

Figure 8:
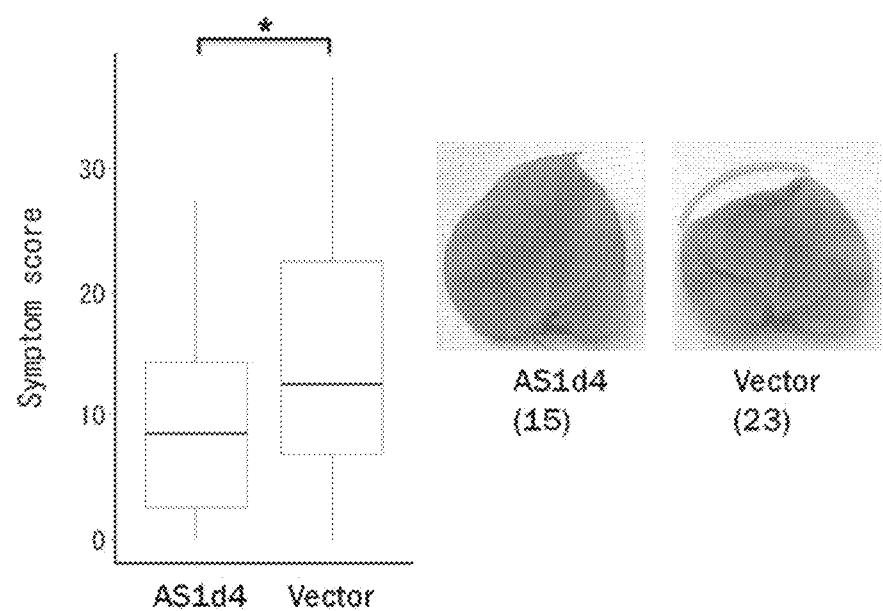
FIG. 8 (left) is a graph indicating the score of a disease symptom (symptom score) caused by βC1, which shows that a disease symptom caused by transiently expressed βC1 was suppressed by transiently expressed decoy peptide d4. The statistical significance was determined by a Wilcoxon rank sum test (n=23, *p<0.05).

FIG. 8 shows the results. From the results of FIG. 8, it is believed that the disease symptom scores in the experimental group into which the decoy peptide d4 gene was co-introduced are significantly lower than those in the control group using the vector. Compared with Test Example 2, the method of Test Example 3 does not require a period for generation of a genetically modified plant, and is thus believed to be a assay system that can evaluate βC1 resistance technologies in a short period of time.

Test Example 4

Interaction Between Decoy Peptides and βC1

Preparation of Decoy Peptides

Various kinds of decoy peptides were purified as follows. The cDNA of each of the decoy peptides was subcloned into the 3'-terminal region of the MBP gene of pMAL-c2x (NEB), which is a maltose-binding protein fusion expression vector. A list of the cDNAs is shown below. Since primers used when GaAS1 D1, GaAS1 D2, GaAS1 D3, and GaAS1 D4 among the decoy peptides derived from cotton AS1 were subcloned into pMAL-c2x had no stop codon, translation was stopped by the stop codon within pMAL-c2x in expression of their recombinant proteins. The obtained plasmid DNAs were introduced into Rosetta (DE3) (Novagen) and routinely cultured to an absorbance (600 nm) of 0.8, and recombinant protein expression was induced by culture with shaking at 16° C. and addition of IPTG (final concentration: 1 mM). The MBP-fused proteins were affinity-purified using MBPTrap HP (GE). The collected protein solutions were concentrated with a 30 K NMWL Amicon Ultra-4 centrifugal filter unit (Merck Millipore).

Figure 9:
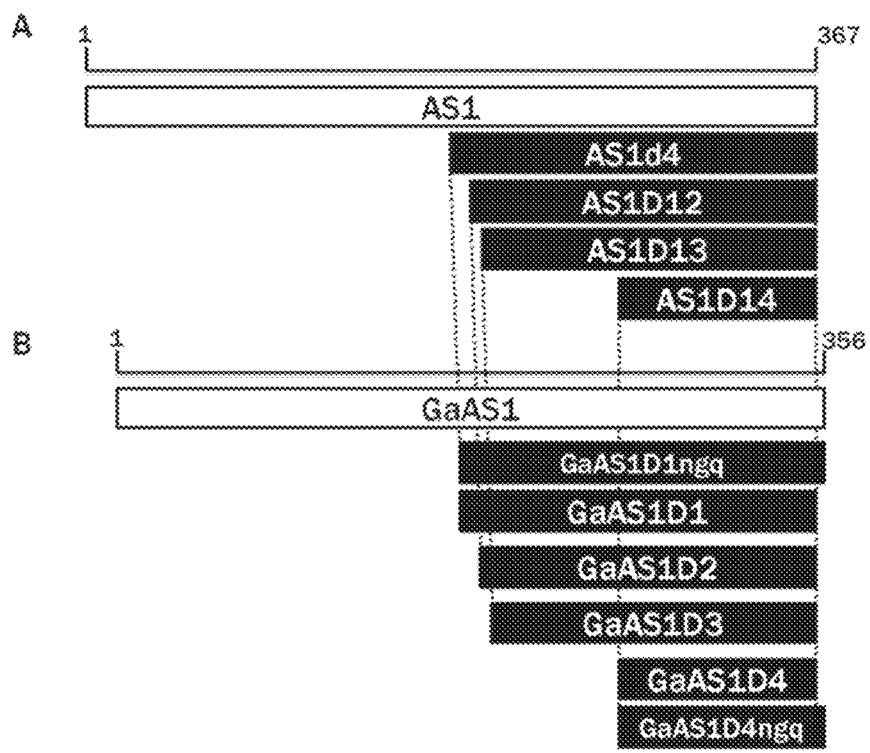
FIG. 9 includes A which shows the positional relationship between the *Arabidopsis thaliana* AS1 protein and decoy peptides, and B which shows the positional relationship between the cotton AS1 protein and decoy peptides.

The decoy peptides derived from cotton AS1 were designed based on the amino acid sequences of decoy peptides derived from *Arabidopsis thaliana* AS1. More specifically, the amino acid sequence of *Arabidopsis thaliana* AS1 was aligned with the amino acid sequence of cotton AS1, and GaAS1D1, GaAS1D2, GaAS1D3, and GaAS1D4 were designed as decoy peptides derived from cotton AS1 corresponding to AS1d4, AS1D12, AS1D13, and AS1D14, which are decoy peptides derived from *Arabidopsis thaliana* (FIG. 9). Further, GaAS1D1ngq and GaAS1D4ngq were designed as decoy peptides in which three amino acids (n-g-q=asparagine-glycine-glutamine) on the C-terminal side in cotton AS1 were added.

MBP-Fused Proteins

Decoy Peptides Derived from *Arabidopsis thaliana* AS1

Position (corresponding amino acid position in *Arabidopsis thaliana* AS1)

AS1 D12 Met-190-367 (SEQ ID NO: 12)
AS1 D13 Met-196-367 (SEQ ID NO: 13)
AS1 D14 Met-267-367 (SEQ ID NO: 14)

Decoy Peptides Derived from Cotton AS1

Position (corresponding amino acid position in *Gossypium arboreum* AS1)

GaAS1 D1 Met-172-353 (SEQ ID NO: 78)
GaAS1 D2 Met-182-353 (SEQ ID NO: 79)
GaAS1 D3 Met-188-353 (SEQ ID NO: 80)
GaAS1 D4 Met-252-353 (SEQ ID NO: 81)
GaAS1 D1ngq Met-172-356 (SEQ ID NO: 15)
GaAS1 D4ngq Met-252-356 (SEQ ID NO: 18)

A GST-fused βC1 protein was prepared by the method shown in Test Example 1.

In Vitro Pulldown Assays

Experiments for interaction between the various kinds of decoy peptides and the βC1 protein derived from Cotton leaf curl virus were performed as follows. 2 μg of GST-βC1-CLCuMB and an equal amount of each of the various kinds of MBP-fused decoy peptides were mixed in pulldown buffer (50 mM Tris-HCl at pH 7.5/100 mM NaCl/0.25% Triton X-100/35 mM thioglycerol) at room temperature for 2 hours. At this time, the supernatants were sampled as input proteins, an equal amount of 2×SDS-PAGE sample buffer was added, and the mixtures were freeze-preserved as input samples. Subsequently, 25 μL of Glutathione Sepharose HP beads (GE) was added, followed by shaking at room temperature for 1 hour. Centrifugation was performed with a small-sized centrifuge at about 5,000 rpm for 30 seconds, the beads were washed with pulldown buffer six times, 25 μL of 2×SDS-PAGE sample buffer was added, and the mixtures were freeze-preserved as pulldown samples.

To detect AS1 that interacted with βC1, proteins co-precipitated with the beads were subjected to SDS-PAGE (6% acrylamide gel), and immunoblotting was performed using an anti-MBP monoclonal antibody (HRP conjugated, NEB) and Amersham ECL Prime (GE). To confirm that these kinds of proteins had been used in equal amounts, the same membrane was regenerated, and immunoblotting was also performed using an anti-GST-tag polyclonal antibody (MBL). Further, for detection of the input samples, immunoblotting was performed in a manner similar to that for the samples co-precipitated with the beads.

Figure 10:
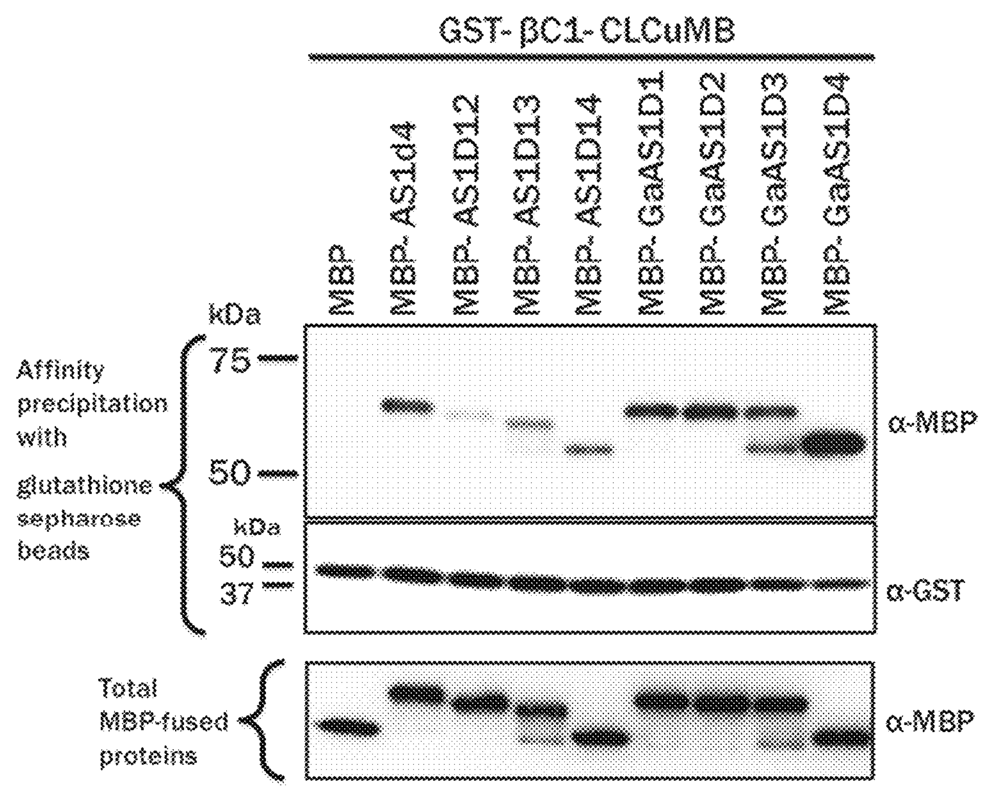
FIG. 10 shows pictures indicating the results of experiments for interaction between decoy peptides derived from *Arabidopsis thaliana* AS1 (AS1d4, AS1D12, AS1D13, and AS1D14) and decoy peptides derived from cotton AS1 (GaAS1D1, GaAS1D2, GaAS1D3, and GaAS1D4), and the βC1 protein derived from Cotton leaf curl virus. Samples co-precipitated with beads to be bound to GST were detected with an anti-MBP antibody (top) and an anti-GST antibody (middle). The bottom picture shows detection of the input proteins with an anti-MBP antibody. The top picture shows interaction between the βC1 protein and the decoy peptides. The bottom two pictures show that these kinds of proteins were added in equal amounts.
Figure 11:
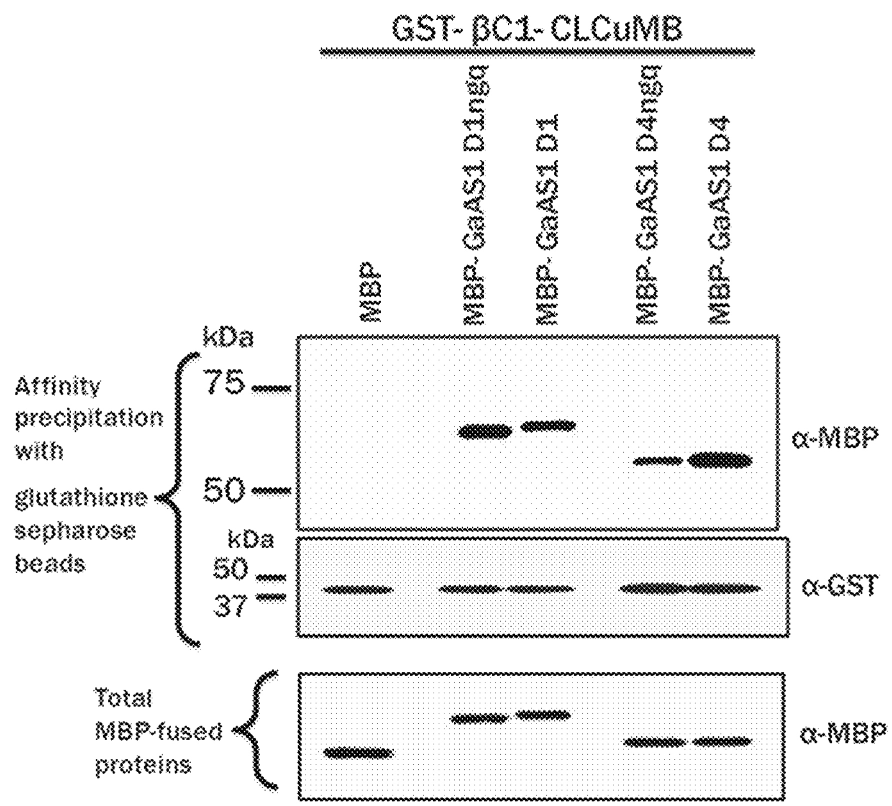
FIG. 11 shows pictures indicating the results of experiments for interaction between decoy peptides derived from cotton AS1 (GaAS1D1ngq, GaAS1D1, GaAS1D4ngq, and GaAS1D4) and the βC1 protein derived from Cotton leaf curl virus. Samples co-precipitated with beads to be bound to GST were detected with an anti-MBP antibody (top) and an anti-GST antibody (middle). The bottom picture shows detection of the input proteins with an anti-MBP antibody. The top picture shows interaction between the βC1 protein and the decoy peptides. The bottom two pictures show that these kinds of proteins were added in equal amounts.

FIGS. 10 and 11 show the results of the experiments using the GST-fused βC1 protein derived from Cotton leaf curl virus and the various kinds of MBP-fused decoy peptides. The results of the in vitro pulldown assays in FIG. 10 revealed that interaction between each of AS1d4, AS1D12, AS1D13, AS1D14, GaAS1D1, GaAS1D2, GaAS1D3, and GaAS1D4, which are decoy peptides, and the βC1 protein derived from Cotton leaf curl virus was detected. The results in FIG. 11 revealed that interaction between each of GaAS1D1ngq, GaAS1D1, GaAS1D4ngq, and GaAS1D4, which are decoy peptides, and the βC1 protein derived from Cotton leaf curl virus was detected.

Test Example 5

Experiments for Confirming Effect of Decoy Peptides Derived from *Arabidopsis thaliana* AS1 and Cotton AS1 in Plant The DNA constructs for decoy peptides used for this experiment were obtained by subcloning each of cDNAs of decoy peptides derived from *Arabidopsis thaliana* (AS1d4 and AS1D14) and decoy peptides derived from cotton AS1 (GaAS1, GaAS1D1ngq, and GaAS1D4ngq) onto a Bin19-based binary vector such that it was controlled by a CaMV35S promoter and a NOS terminator. The same βC1 gene as used in Test Example 3 was used.

These DNA constructs were used for *Agrobacterium* transformation. The resulting Agrobacteria were cultured with shaking in LB medium supplemented with a selection antibiotic at 30° C. for 24 hours. The cells were collected at 3,000 rpm for 15 minutes with a Hitachi tabletop centrifuge, and resuspended with infiltration buffer (1 mM MES pH 5.6, 1 mM $MgCl_2$, 100 μM Acetosyringone). After adjusting the absorbance (600 nm) to 1.0, the suspension containing the βC1 gene and the suspension containing a decoy peptide gene to be co-introduced were mixed in a ratio of the suspension containing the βC1 gene:the suspension containing the decoy peptide gene to be co-introduced=1:9. For comparison with the decoy peptide gene to be co-introduced, an *Agrobacterium* mixture containing vector DNA (pBI101) was prepared, and the suspension containing the βC1 gene and the suspension containing the vector were mixed in a ratio of the suspension containing the βC1 gene:the suspension containing the vector=1:9. Each inoculum was injected using a 1 mL-syringe into an area that was 70% or more of two upper expanded leaves of *Nicotiana benthamiana* cultivated for one month.

From 12 days after the inoculation, the symptom scores of the leaf curl symptom on the first to fifth upper leaves from the inoculated leaves were recorded. What percentage of the outer circumference whose outer peripheral edge portion developed a leaf curl symptom in each of the five leaves per plant was investigated, and rated on a scale of 0 to 100. The average value of the scores in a plant was regarded as the symptom score of the plant. Multiple comparisons using Dunnett's method were performed with software R version 3.1.0.

Figure 12:
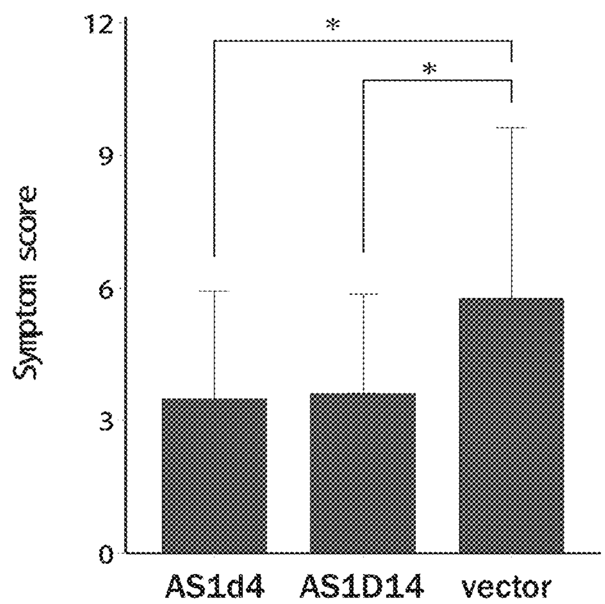
FIG. 12 is a graph indicating the score of a disease symptom (symptom score) caused by βC1 in plant *Nicotiana benthamiana*, which shows that a disease symptom caused by transiently expressed βC1 was suppressed by each of transiently expressed decoy peptides (AS1d4 and AS1D14). Black bars indicate the average values in experimental groups, and error bars are standard deviations. Statistical significance was determined by multiple comparisons using Dunnett's method (n=20, *p<0.05 (comparisons with control)).
Figure 13:
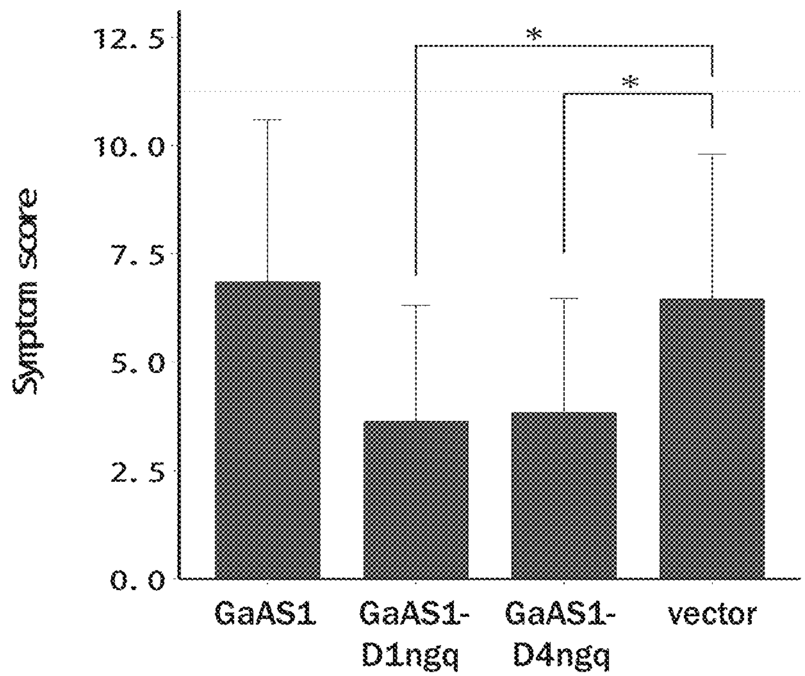
FIG. 13 is a graph indicating the score of a disease symptom (symptom score) caused by βC1 in plant *Nicotiana benthamiana*, which shows that a disease symptom caused by transiently expressed βC1 was suppressed by each of transiently expressed decoy peptides (GaAS1D1 ngq and GaAS1D4ngq). Black bars indicate the average values in experimental groups, and error bars are standard deviations. Statistical significance was determined by multiple comparisons using Dunnett's method (n=20, *p<0.05 (comparisons with control)).

FIGS. 12 and 13 show the experimental results. The results in FIG. 12 revealed that the disease symptom scores in the experimental group using decoy peptide AS1D14 derived from *Arabidopsis thaliana* AS1 were significantly lower than those in the experimental group using the vector, as in the experimental group using AS1d4. The results in FIG. 13 revealed that the disease symptom scores in the experimental group into which decoy peptide GaAS1D1ngq or GaAS1D4ngq gene derived from cotton AS1 was co-introduced were significantly lower than those in the experimental group using the vector. However, when the cotton AS1 gene (GaAS1) itself was co-introduced, no differences from the control group using the vector in terms of disease symptom score were detected.

Test Example 6

Experiment for Interaction Between Soybean AS1 and βC1

Preparation of Recombinant Protein

A soybean AS1 (GmAS1) recombinant protein was purified as follows. The cDNA of GmAS1 (full length: 361 amino acids) was subcloned into the 3'-terminal region of the MBP gene of pMAL-c2x (NEB), which is a maltose-binding protein fusion expression vector. The obtained plasmid DNA was introduced into Rosetta (DE3) (Novagen) and routinely cultured to an absorbance (600 nm) of 0.8, and recombinant protein expression was induced by culture with shaking at 16° C. and addition of IPTG (final concentration: 1 mM). The MBP-fused protein was affinity-purified using MBPTrap HP (GE). The collected protein solution was concentrated with a 30K NMWL Amicon Ultra-4 centrifugal filter unit (Merck Millipore).

A GST-fused βC1 protein was prepared by the method shown in Test Example 1.

In Vitro Pulldown Assays

An experiment for interaction between GmAS1 and the βC1 protein derived from Cotton leaf curl virus was performed as follows. 2 μg of GST-βC1-CLCuMB and an equal amount of MBP-GmAS1 were mixed in pulldown buffer (50 mM Tris-HCl at pH 7.5/100 mM NaCl/0.25% Triton X-100/35 mM thioglycerol) at room temperature for 2 hours. At the same time, a sample obtained by using GST-βC1-CLCuMB in an amount of 1/10, i.e., 0.2 μg, and MBP-GmAS1 in an amount of 2 μg was prepared to confirm amount dependency. At this time, the supernatants were sampled as input proteins, an equal amount of 2×SDS-PAGE sample buffer was added, and the mixtures were freeze-preserved as input samples. Subsequently, 40 μL of anti-MBP magnetic beads (NEB) was added, followed by shaking at room temperature for 1 hour. Thereafter, the beads were washed with pulldown buffer six times while immobilizing the beads in the tubes with a magnet, 25 μL of 2×SDS-PAGE sample buffer was added, and the mixtures were freeze-preserved as pulldown samples.

To detect GST-βC1-CLCuMB that interacted with MBP-GmAS1, proteins co-precipitated with the beads were subjected to SDS-PAGE (6% acrylamide gel), and immunoblotting was performed using an anti-GST-tag polyclonal antibody (MBL), anti-Rabbit IgG, HRP-Linked Whole Ab Donkey (GE), and Amersham ECL Prime (GE). To confirm that these kinds of proteins had been used in equal amounts, the same membrane was regenerated, and immunoblotting was also performed using an anti-MBP monoclonal antibody (HRP conjugated, NEB). Further, for detection of the input samples, immunoblotting was performed in a manner similar to that for the samples co-precipitated with the beads.

Figure 14:
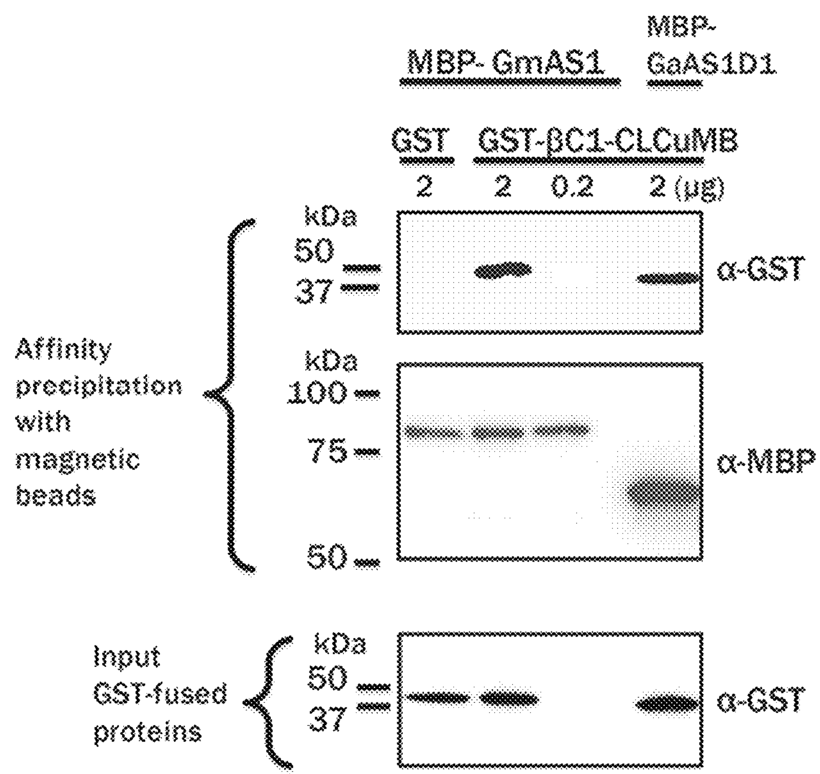
FIG. 14 shows pictures indicating the results of an experiment for interaction between the soybean AS1 protein (GmAS1) and the βC1 protein derived from Cotton leaf curl virus (βC1-CLCuMB). A decoy peptide derived from cotton AS1, GaAS1D1, is used as a positive control. Samples co-precipitated with magnetic beads to be bound to MBP were detected with an anti-GST antibody (top) and an anti-MBP antibody (middle). The bottom picture shows detection of the input proteins with an anti-GST antibody. The top picture shows interaction between the βC1 protein and the GmAS1 protein. The bottom two pictures show that these kinds of proteins were added in equal amounts. In only the third lane from left, i.e., lane 3, the GST-βC1-CLCuMB protein was used in an amount of 1/10 of the amount in each of the other cases to confirm amount dependency.

FIG. 14 shows the experimental results. The results revealed that co-precipitation of MBP-GmAS1 with GST-βC1-CLCuMB was detected as in the case performed using MBP-GaAS1D1 as a positive control. Additionally, its signal intensity was dependent on the amount of GST-βC1-CLCuMB. In the sample in which the amount of GST-βC1-CLCuMB was reduced to 1/10, the input protein of GST-βC1-CLCuMB could not be detected in this experiment. This is considered to be because it was an amount close to the detection limit in this experimental system. The results of this experiment indicate interaction between AS1 of a plant of the family Fabaceae and βC1 derived from Cotton leaf curl virus, which infects plants of the family Malvaceae.

Viruses are known to evolve and gain new hosts. For example, βC1 derived from Tomato leaf curl virus has been recently reported to cause Cotton leaf curl disease in cotton (e.g., Sattar M N, Iqbal Z, Tahir M N and Ullah S (2017) The prediction of a new CLCuD epidemic in the Old World. Front. Microbiol. 8:631. doi:10.3389/fmicb.2017.00631). This means that crop losses caused by pathogenic factor βC1 may not be limited to currently reported crop diseases and, in the future, may spread to crops in which the crop damage has not been reported at present. As an example thereof, Test Example 6 indicates that AS1 of soybean, a crop of the family Fabaceae, (GmAS1), in which diseases caused by βC1 have not yet been reported, interacts with the βC1 protein derived from Cotton leaf curl virus. Thus, even if a viral disease caused by βC1 occurs in crops like soybean, the decoy technology disclosed in the present invention is expected to be effective.

The invention claimed is:

1. A method for reducing a disease symptom caused by a virus that comprises βC1 and belongs to the family Geminiviridae, the method comprising:

introducing into a plant a nucleic acid encoding a peptide fragment of ASYMMETRIC LEAVES1 (AS1) of SEQ ID NO: 71, wherein the length of the peptide fragment of AS1 is 16 to 63% of the full length of SEQ ID NO: 71, in terms of the number of amino acid residues.

2. A method for reducing a disease symptom caused by a virus that comprises βC1 and belongs to the family Geminiviridae, the method comprising:

introducing into a plant nucleic acid encoding a peptide set forth in the following (A) or (B):

(A) a peptide consisting of the amino acid sequence represented by any one of SEQ ID NOs: 3 to 18 and 78 to 81, or (B) a peptide consisting of the amino acid sequence represented by any one of SEQ ID NOs: 3 to 18, and 78 to 81 in which 1 to a total of 10 amino acids are deleted, substituted, inserted, and/or added, wherein the peptide set forth in (A) or (B) comprises at least one motif selected from the group consisting of a PSVTL(S/T)L motif of SEQ ID NO: 82 and a coiled-coil motif.

3. The method of claim 2, wherein the nucleic acid encodes the peptide set forth in (A).

4. The method of claim 2, wherein the nucleic acid encodes the peptide set forth in (B).

5. The method of claim 1, wherein the peptide fragment comprises at least one motif selected from the group consisting of a leucine zipper motif, a PSVTL(S/T)L motif of SEQ ID NO: 82, and a coiled-coil motif.

6. The method of claim 1, wherein the peptide fragment of AS1 has one or more amino acids added to one or both terminals of the peptide fragment.

* * * * *

```
                              SEQUENCE LISTING

<160> NUMBER OF SEQ ID NOS: 82

<210> SEQ ID NO 1
<211> LENGTH: 145
<212> TYPE: PRT
<213> ORGANISM: Arabidopsis thaliana

<400> SEQUENCE: 1

Met Lys Glu Arg Gln Arg Trp Ser Gly Glu Glu Asp Ala Leu Leu Arg
1               5                   10                  15

Ala Tyr Val Arg Gln Phe Gly Pro Arg Glu Trp His Leu Val Ser Glu
            20                  25                  30

Arg Met Asn Lys Pro Leu Asn Arg Asp Ala Lys Ser Cys Leu Glu Arg
        35                  40                  45

Trp Lys Asn Tyr Leu Lys Pro Gly Ile Lys Lys Gly Ser Leu Thr Glu
    50                  55                  60

Glu Glu Gln Arg Leu Val Ile Arg Leu Gln Glu Lys His Gly Asn Lys
65                  70                  75                  80

Trp Lys Lys Ile Ala Ala Glu Val Pro Gly Arg Thr Ala Lys Arg Leu
                85                  90                  95

Gly Lys Trp Trp Glu Val Phe Lys Glu Lys Gln Gln Arg Glu Glu Lys
            100                 105                 110

Glu Ser Asn Lys Arg Val Glu Pro Ile Asp Glu Ser Lys Tyr Asp Arg
        115                 120                 125

Ile Leu Glu Ser Phe Ala Glu Lys Leu Val Lys Glu Arg Ser Asn Val
    130                 135                 140

Val
145


<210> SEQ ID NO 2
<211> LENGTH: 179
<212> TYPE: PRT
<213> ORGANISM: Arabidopsis thaliana

<400> SEQUENCE: 2

Met Lys Glu Arg Gln Arg Trp Ser Gly Glu Glu Asp Ala Leu Leu Arg
1               5                   10                  15

Ala Tyr Val Arg Gln Phe Gly Pro Arg Glu Trp His Leu Val Ser Glu
            20                  25                  30

Arg Met Asn Lys Pro Leu Asn Arg Asp Ala Lys Ser Cys Leu Glu Arg
        35                  40                  45
```

```
Trp Lys Asn Tyr Leu Lys Pro Gly Ile Lys Lys Gly Ser Leu Thr Glu
    50                  55                  60

Glu Glu Gln Arg Leu Val Ile Arg Leu Gln Glu Lys His Gly Asn Lys
65                  70                  75                  80

Trp Lys Lys Ile Ala Ala Glu Val Pro Gly Arg Thr Ala Lys Arg Leu
                85                  90                  95

Gly Lys Trp Trp Glu Val Phe Lys Glu Lys Gln Gln Arg Glu Glu Lys
            100                 105                 110

Glu Ser Asn Lys Arg Val Glu Pro Ile Asp Glu Ser Lys Tyr Asp Arg
        115                 120                 125

Ile Leu Glu Ser Phe Ala Glu Lys Leu Val Lys Glu Arg Ser Asn Val
    130                 135                 140

Val Pro Ala Ala Ala Ala Ala Ala Thr Val Val Met Ala Asn Ser Asn
145                 150                 155                 160

Gly Gly Phe Leu His Ser Glu Gln Gln Val Gln Pro Pro Asn Pro Val
                165                 170                 175

Ile Pro Pro


<210> SEQ ID NO 3
<211> LENGTH: 146
<212> TYPE: PRT
<213> ORGANISM: Arabidopsis thaliana

<400> SEQUENCE: 3

Met Lys Gln Gln Arg Glu Glu Lys Glu Ser Asn Lys Arg Val Glu Pro
1               5                   10                  15

Ile Asp Glu Ser Lys Tyr Asp Arg Ile Leu Glu Ser Phe Ala Glu Lys
            20                  25                  30

Leu Val Lys Glu Arg Ser Asn Val Val Pro Ala Ala Ala Ala Ala Ala
        35                  40                  45

Thr Val Val Met Ala Asn Ser Asn Gly Gly Phe Leu His Ser Glu Gln
    50                  55                  60

Gln Val Gln Pro Pro Asn Pro Val Ile Pro Pro Trp Leu Ala Thr Ser
65                  70                  75                  80

Asn Asn Gly Asn Asn Val Val Ala Arg Pro Pro Ser Val Thr Leu Thr
                85                  90                  95

Leu Ser Pro Ser Thr Val Ala Ala Ala Ala Pro Gln Pro Pro Ile Pro
            100                 105                 110

Trp Leu Gln Gln Gln Gln Pro Glu Arg Ala Glu Asn Gly Pro Gly Gly
        115                 120                 125

Leu Val Leu Gly Ser Met Met Pro Ser Cys Ser Gly Ser Ser Glu Ser
    130                 135                 140

Val Phe
145


<210> SEQ ID NO 4
<211> LENGTH: 189
<212> TYPE: PRT
<213> ORGANISM: Arabidopsis thaliana

<400> SEQUENCE: 4

Met Trp Leu Ala Thr Ser Asn Asn Gly Asn Asn Val Val Ala Arg Pro
1               5                   10                  15

Pro Ser Val Thr Leu Thr Leu Ser Pro Ser Thr Val Ala Ala Ala Ala
            20                  25                  30

Pro Gln Pro Pro Ile Pro Trp Leu Gln Gln Gln Gln Pro Glu Arg Ala
```

```
        35                  40                  45

Glu Asn Gly Pro Gly Gly Leu Val Leu Gly Ser Met Met Pro Ser Cys
    50                  55                  60

Ser Gly Ser Ser Glu Ser Val Phe Leu Ser Glu Leu Val Glu Cys Cys
65                  70                  75                  80

Arg Glu Leu Glu Glu Gly His Arg Ala Trp Ala Asp His Lys Lys Glu
                85                  90                  95

Ala Ala Trp Arg Leu Arg Arg Leu Glu Leu Gln Leu Glu Ser Glu Lys
            100                 105                 110

Thr Cys Arg Gln Arg Glu Lys Met Glu Glu Ile Glu Ala Lys Met Lys
        115                 120                 125

Ala Leu Arg Glu Glu Gln Lys Asn Ala Met Glu Lys Ile Glu Gly Glu
    130                 135                 140

Tyr Arg Glu Gln Leu Val Gly Leu Arg Arg Asp Ala Glu Ala Lys Asp
145                 150                 155                 160

Gln Lys Leu Ala Asp Gln Trp Thr Ser Arg His Ile Arg Leu Thr Lys
                165                 170                 175

Phe Leu Glu Gln Gln Met Gly Cys Arg Leu Asp Arg Pro
            180                 185


<210> SEQ ID NO 5
<211> LENGTH: 224
<212> TYPE: PRT
<213> ORGANISM: Arabidopsis thaliana

<400> SEQUENCE: 5

Met Lys Lys Gly Ser Leu Thr Glu Glu Glu Gln Arg Leu Val Ile Arg
1               5                   10                  15

Leu Gln Glu Lys His Gly Asn Lys Trp Lys Lys Ile Ala Ala Glu Val
            20                  25                  30

Pro Gly Arg Thr Ala Lys Arg Leu Gly Lys Trp Trp Glu Val Phe Lys
        35                  40                  45

Glu Lys Gln Gln Arg Glu Glu Lys Glu Ser Asn Lys Arg Val Glu Pro
    50                  55                  60

Ile Asp Glu Ser Lys Tyr Asp Arg Ile Leu Glu Ser Phe Ala Glu Lys
65                  70                  75                  80

Leu Val Lys Glu Arg Ser Asn Val Val Pro Ala Ala Ala Ala Ala Ala
                85                  90                  95

Thr Val Val Met Ala Asn Ser Asn Gly Gly Phe Leu His Ser Glu Gln
            100                 105                 110

Gln Val Gln Pro Pro Asn Pro Val Ile Pro Pro Trp Leu Ala Thr Ser
        115                 120                 125

Asn Asn Gly Asn Asn Val Val Ala Arg Pro Pro Ser Val Thr Leu Thr
    130                 135                 140

Leu Ser Pro Ser Thr Val Ala Ala Ala Ala Pro Gln Pro Pro Ile Pro
145                 150                 155                 160

Trp Leu Gln Gln Gln Gln Pro Glu Arg Ala Glu Asn Gly Pro Gly Gly
                165                 170                 175

Leu Val Leu Gly Ser Met Met Pro Ser Cys Ser Gly Ser Ser Glu Ser
            180                 185                 190

Val Phe Leu Ser Glu Leu Val Glu Cys Cys Arg Glu Leu Glu Glu Gly
        195                 200                 205

His Arg Ala Trp Ala Asp His Lys Lys Glu Ala Ala Trp Arg Leu Arg
    210                 215                 220
```

```
<210> SEQ ID NO 6
<211> LENGTH: 268
<212> TYPE: PRT
<213> ORGANISM: Arabidopsis thaliana

<400> SEQUENCE: 6

Met Lys Lys Gly Ser Leu Thr Glu Glu Glu Gln Arg Leu Val Ile Arg
1               5                   10                  15

Leu Gln Glu Lys His Gly Asn Lys Trp Lys Lys Ile Ala Ala Glu Val
            20                  25                  30

Pro Gly Arg Thr Ala Lys Arg Leu Gly Lys Trp Trp Glu Val Phe Lys
        35                  40                  45

Glu Lys Gln Gln Arg Glu Glu Lys Glu Ser Asn Lys Arg Val Glu Pro
    50                  55                  60

Ile Asp Glu Ser Lys Tyr Asp Arg Ile Leu Glu Ser Phe Ala Glu Lys
65                  70                  75                  80

Leu Val Lys Glu Arg Ser Asn Val Val Pro Ala Ala Ala Ala Ala Ala
                85                  90                  95

Thr Val Val Met Ala Asn Ser Asn Gly Gly Phe Leu His Ser Glu Gln
            100                 105                 110

Gln Val Gln Pro Pro Asn Pro Val Ile Pro Pro Trp Leu Ala Thr Ser
        115                 120                 125

Asn Asn Gly Asn Asn Val Val Ala Arg Pro Pro Ser Val Thr Leu Thr
    130                 135                 140

Leu Ser Pro Ser Thr Val Ala Ala Ala Ala Pro Gln Pro Pro Ile Pro
145                 150                 155                 160

Trp Leu Gln Gln Gln Gln Pro Glu Arg Ala Glu Asn Gly Pro Gly Gly
                165                 170                 175

Leu Val Leu Gly Ser Met Met Pro Ser Cys Ser Gly Ser Ser Glu Ser
            180                 185                 190

Val Phe Leu Ser Glu Leu Val Glu Cys Cys Arg Glu Leu Glu Glu Gly
        195                 200                 205

His Arg Ala Trp Ala Asp His Lys Lys Glu Ala Ala Trp Arg Leu Arg
    210                 215                 220

Arg Leu Glu Leu Gln Leu Glu Ser Glu Lys Thr Cys Arg Gln Arg Glu
225                 230                 235                 240

Lys Met Glu Glu Ile Glu Ala Lys Met Lys Ala Leu Arg Glu Glu Gln
                245                 250                 255

Lys Asn Ala Met Glu Lys Ile Glu Gly Glu Tyr Arg
            260                 265


<210> SEQ ID NO 7
<211> LENGTH: 311
<212> TYPE: PRT
<213> ORGANISM: Arabidopsis thaliana

<400> SEQUENCE: 7

Met Lys Lys Gly Ser Leu Thr Glu Glu Glu Gln Arg Leu Val Ile Arg
1               5                   10                  15

Leu Gln Glu Lys His Gly Asn Lys Trp Lys Lys Ile Ala Ala Glu Val
            20                  25                  30

Pro Gly Arg Thr Ala Lys Arg Leu Gly Lys Trp Trp Glu Val Phe Lys
        35                  40                  45

Glu Lys Gln Gln Arg Glu Glu Lys Glu Ser Asn Lys Arg Val Glu Pro
    50                  55                  60
```

```
Ile Asp Glu Ser Lys Tyr Asp Arg Ile Leu Glu Ser Phe Ala Glu Lys
65                  70                  75                  80

Leu Val Lys Glu Arg Ser Asn Val Val Pro Ala Ala Ala Ala Ala Ala
                85                  90                  95

Thr Val Val Met Ala Asn Ser Asn Gly Gly Phe Leu His Ser Glu Gln
            100                 105                 110

Gln Val Gln Pro Pro Asn Pro Val Ile Pro Pro Trp Leu Ala Thr Ser
        115                 120                 125

Asn Asn Gly Asn Asn Val Val Ala Arg Pro Pro Ser Val Thr Leu Thr
    130                 135                 140

Leu Ser Pro Ser Thr Val Ala Ala Ala Ala Pro Gln Pro Pro Ile Pro
145                 150                 155                 160

Trp Leu Gln Gln Gln Gln Pro Glu Arg Ala Glu Asn Gly Pro Gly Gly
                165                 170                 175

Leu Val Leu Gly Ser Met Met Pro Ser Cys Ser Gly Ser Ser Glu Ser
            180                 185                 190

Val Phe Leu Ser Glu Leu Val Glu Cys Cys Arg Glu Leu Glu Glu Gly
        195                 200                 205

His Arg Ala Trp Ala Asp His Lys Lys Glu Ala Ala Trp Arg Leu Arg
    210                 215                 220

Arg Leu Glu Leu Gln Leu Glu Ser Glu Lys Thr Cys Arg Gln Arg Glu
225                 230                 235                 240

Lys Met Glu Glu Ile Glu Ala Lys Met Lys Ala Leu Arg Glu Glu Gln
                245                 250                 255

Lys Asn Ala Met Glu Lys Ile Glu Gly Glu Tyr Arg Glu Gln Leu Val
            260                 265                 270

Gly Leu Arg Arg Asp Ala Glu Ala Lys Asp Gln Lys Leu Ala Asp Gln
        275                 280                 285

Trp Thr Ser Arg His Ile Arg Leu Thr Lys Phe Leu Glu Gln Gln Met
    290                 295                 300

Gly Cys Arg Leu Asp Arg Pro
305                 310


<210> SEQ ID NO 8
<211> LENGTH: 187
<212> TYPE: PRT
<213> ORGANISM: Arabidopsis thaliana

<400> SEQUENCE: 8

Met Arg Leu Gly Lys Trp Trp Glu Val Phe Lys Glu Lys Gln Gln Arg
1               5                   10                  15

Glu Glu Lys Glu Ser Asn Lys Arg Val Glu Pro Ile Asp Glu Ser Lys
            20                  25                  30

Tyr Asp Arg Ile Leu Glu Ser Phe Ala Glu Lys Leu Val Lys Glu Arg
        35                  40                  45

Ser Asn Val Val Pro Ala Ala Ala Ala Ala Ala Thr Val Val Met Ala
    50                  55                  60

Asn Ser Asn Gly Gly Phe Leu His Ser Glu Gln Gln Val Gln Pro Pro
65                  70                  75                  80

Asn Pro Val Ile Pro Pro Trp Leu Ala Thr Ser Asn Asn Gly Asn Asn
                85                  90                  95

Val Val Ala Arg Pro Pro Ser Val Thr Leu Thr Leu Ser Pro Ser Thr
            100                 105                 110

Val Ala Ala Ala Ala Pro Gln Pro Pro Ile Pro Trp Leu Gln Gln Gln
        115                 120                 125
```

```
Gln Pro Glu Arg Ala Glu Asn Gly Pro Gly Gly Leu Val Leu Gly Ser
    130                 135                 140

Met Met Pro Ser Cys Ser Gly Ser Ser Glu Ser Val Phe Leu Ser Glu
145                 150                 155                 160

Leu Val Glu Cys Cys Arg Glu Leu Glu Glu Gly His Arg Ala Trp Ala
                165                 170                 175

Asp His Lys Lys Glu Ala Ala Trp Arg Leu Arg
            180                 185


<210> SEQ ID NO 9
<211> LENGTH: 231
<212> TYPE: PRT
<213> ORGANISM: Arabidopsis thaliana

<400> SEQUENCE: 9

Met Arg Leu Gly Lys Trp Trp Glu Val Phe Lys Glu Lys Gln Gln Arg
1               5                   10                  15

Glu Glu Lys Glu Ser Asn Lys Arg Val Glu Pro Ile Asp Glu Ser Lys
            20                  25                  30

Tyr Asp Arg Ile Leu Glu Ser Phe Ala Glu Lys Leu Val Lys Glu Arg
        35                  40                  45

Ser Asn Val Val Pro Ala Ala Ala Ala Ala Ala Thr Val Val Met Ala
    50                  55                  60

Asn Ser Asn Gly Gly Phe Leu His Ser Glu Gln Gln Val Gln Pro Pro
65                  70                  75                  80

Asn Pro Val Ile Pro Pro Trp Leu Ala Thr Ser Asn Asn Gly Asn Asn
                85                  90                  95

Val Val Ala Arg Pro Pro Ser Val Thr Leu Thr Leu Ser Pro Ser Thr
            100                 105                 110

Val Ala Ala Ala Ala Pro Gln Pro Pro Ile Pro Trp Leu Gln Gln Gln
        115                 120                 125

Gln Pro Glu Arg Ala Glu Asn Gly Pro Gly Gly Leu Val Leu Gly Ser
    130                 135                 140

Met Met Pro Ser Cys Ser Gly Ser Ser Glu Ser Val Phe Leu Ser Glu
145                 150                 155                 160

Leu Val Glu Cys Cys Arg Glu Leu Glu Glu Gly His Arg Ala Trp Ala
                165                 170                 175

Asp His Lys Lys Glu Ala Ala Trp Arg Leu Arg Arg Leu Glu Leu Gln
            180                 185                 190

Leu Glu Ser Glu Lys Thr Cys Arg Gln Arg Glu Lys Met Glu Glu Ile
        195                 200                 205

Glu Ala Lys Met Lys Ala Leu Arg Glu Glu Gln Lys Asn Ala Met Glu
    210                 215                 220

Lys Ile Glu Gly Glu Tyr Arg
225                 230


<210> SEQ ID NO 10
<211> LENGTH: 274
<212> TYPE: PRT
<213> ORGANISM: Arabidopsis thaliana

<400> SEQUENCE: 10

Met Arg Leu Gly Lys Trp Trp Glu Val Phe Lys Glu Lys Gln Gln Arg
1               5                   10                  15

Glu Glu Lys Glu Ser Asn Lys Arg Val Glu Pro Ile Asp Glu Ser Lys
            20                  25                  30
```

```
Tyr Asp Arg Ile Leu Glu Ser Phe Ala Glu Lys Leu Val Lys Glu Arg
        35                  40                  45

Ser Asn Val Val Pro Ala Ala Ala Ala Ala Ala Thr Val Val Met Ala
    50                  55                  60

Asn Ser Asn Gly Gly Phe Leu His Ser Glu Gln Gln Val Gln Pro Pro
65                  70                  75                  80

Asn Pro Val Ile Pro Pro Trp Leu Ala Thr Ser Asn Asn Gly Asn Asn
                85                  90                  95

Val Val Ala Arg Pro Pro Ser Val Thr Leu Thr Leu Ser Pro Ser Thr
            100                 105                 110

Val Ala Ala Ala Ala Pro Gln Pro Pro Ile Pro Trp Leu Gln Gln Gln
        115                 120                 125

Gln Pro Glu Arg Ala Glu Asn Gly Pro Gly Gly Leu Val Leu Gly Ser
    130                 135                 140

Met Met Pro Ser Cys Ser Gly Ser Ser Glu Ser Val Phe Leu Ser Glu
145                 150                 155                 160

Leu Val Glu Cys Cys Arg Glu Leu Glu Glu Gly His Arg Ala Trp Ala
                165                 170                 175

Asp His Lys Lys Glu Ala Ala Trp Arg Leu Arg Arg Leu Glu Leu Gln
            180                 185                 190

Leu Glu Ser Glu Lys Thr Cys Arg Gln Arg Glu Lys Met Glu Glu Ile
        195                 200                 205

Glu Ala Lys Met Lys Ala Leu Arg Glu Glu Gln Lys Asn Ala Met Glu
    210                 215                 220

Lys Ile Glu Gly Glu Tyr Arg Glu Gln Leu Val Gly Leu Arg Arg Asp
225                 230                 235                 240

Ala Glu Ala Lys Asp Gln Lys Leu Ala Asp Gln Trp Thr Ser Arg His
                245                 250                 255

Ile Arg Leu Thr Lys Phe Leu Glu Gln Gln Met Gly Cys Arg Leu Asp
            260                 265                 270

Arg Pro


<210> SEQ ID NO 11
<211> LENGTH: 212
<212> TYPE: PRT
<213> ORGANISM: Arabidopsis thaliana

<400> SEQUENCE: 11

Met Ala Asn Ser Asn Gly Gly Phe Leu His Ser Glu Gln Gln Val Gln
1               5                   10                  15

Pro Pro Asn Pro Val Ile Pro Pro Trp Leu Ala Thr Ser Asn Asn Gly
            20                  25                  30

Asn Asn Val Val Ala Arg Pro Pro Ser Val Thr Leu Thr Leu Ser Pro
        35                  40                  45

Ser Thr Val Ala Ala Ala Ala Pro Gln Pro Pro Ile Pro Trp Leu Gln
    50                  55                  60

Gln Gln Gln Pro Glu Arg Ala Glu Asn Gly Pro Gly Gly Leu Val Leu
65                  70                  75                  80

Gly Ser Met Met Pro Ser Cys Ser Gly Ser Ser Glu Ser Val Phe Leu
                85                  90                  95

Ser Glu Leu Val Glu Cys Cys Arg Glu Leu Glu Glu Gly His Arg Ala
            100                 105                 110

Trp Ala Asp His Lys Lys Glu Ala Ala Trp Arg Leu Arg Arg Leu Glu
        115                 120                 125
```

```
Leu Gln Leu Glu Ser Glu Lys Thr Cys Arg Gln Arg Glu Lys Met Glu
    130                 135                 140

Glu Ile Glu Ala Lys Met Lys Ala Leu Arg Glu Glu Gln Lys Asn Ala
145                 150                 155                 160

Met Glu Lys Ile Glu Gly Glu Tyr Arg Glu Gln Leu Val Gly Leu Arg
                165                 170                 175

Arg Asp Ala Glu Ala Lys Asp Gln Lys Leu Ala Asp Gln Trp Thr Ser
            180                 185                 190

Arg His Ile Arg Leu Thr Lys Phe Leu Glu Gln Gln Met Gly Cys Arg
        195                 200                 205

Leu Asp Arg Pro
    210


<210> SEQ ID NO 12
<211> LENGTH: 179
<212> TYPE: PRT
<213> ORGANISM: Arabidopsis thaliana

<400> SEQUENCE: 12

Met Val Val Ala Arg Pro Pro Ser Val Thr Leu Thr Leu Ser Pro Ser
1               5                   10                  15

Thr Val Ala Ala Ala Ala Pro Gln Pro Pro Ile Pro Trp Leu Gln Gln
            20                  25                  30

Gln Gln Pro Glu Arg Ala Glu Asn Gly Pro Gly Gly Leu Val Leu Gly
        35                  40                  45

Ser Met Met Pro Ser Cys Ser Gly Ser Ser Glu Ser Val Phe Leu Ser
    50                  55                  60

Glu Leu Val Glu Cys Cys Arg Glu Leu Glu Glu Gly His Arg Ala Trp
65                  70                  75                  80

Ala Asp His Lys Lys Glu Ala Ala Trp Arg Leu Arg Arg Leu Glu Leu
                85                  90                  95

Gln Leu Glu Ser Glu Lys Thr Cys Arg Gln Arg Glu Lys Met Glu Glu
            100                 105                 110

Ile Glu Ala Lys Met Lys Ala Leu Arg Glu Glu Gln Lys Asn Ala Met
        115                 120                 125

Glu Lys Ile Glu Gly Glu Tyr Arg Glu Gln Leu Val Gly Leu Arg Arg
    130                 135                 140

Asp Ala Glu Ala Lys Asp Gln Lys Leu Ala Asp Gln Trp Thr Ser Arg
145                 150                 155                 160

His Ile Arg Leu Thr Lys Phe Leu Glu Gln Gln Met Gly Cys Arg Leu
                165                 170                 175

Asp Arg Pro


<210> SEQ ID NO 13
<211> LENGTH: 173
<212> TYPE: PRT
<213> ORGANISM: Arabidopsis thaliana

<400> SEQUENCE: 13

Met Ser Val Thr Leu Thr Leu Ser Pro Ser Thr Val Ala Ala Ala Ala
1               5                   10                  15

Pro Gln Pro Pro Ile Pro Trp Leu Gln Gln Gln Gln Pro Glu Arg Ala
            20                  25                  30

Glu Asn Gly Pro Gly Gly Leu Val Leu Gly Ser Met Met Pro Ser Cys
        35                  40                  45
```

```
Ser Gly Ser Ser Glu Ser Val Phe Leu Ser Glu Leu Val Glu Cys Cys
    50                  55                  60

Arg Glu Leu Glu Glu Gly His Arg Ala Trp Ala Asp His Lys Lys Glu
65                  70                  75                  80

Ala Ala Trp Arg Leu Arg Arg Leu Glu Leu Gln Leu Glu Ser Glu Lys
                85                  90                  95

Thr Cys Arg Gln Arg Glu Lys Met Glu Glu Ile Glu Ala Lys Met Lys
            100                 105                 110

Ala Leu Arg Glu Glu Gln Lys Asn Ala Met Glu Lys Ile Glu Gly Glu
        115                 120                 125

Tyr Arg Glu Gln Leu Val Gly Leu Arg Arg Asp Ala Glu Ala Lys Asp
    130                 135                 140

Gln Lys Leu Ala Asp Gln Trp Thr Ser Arg His Ile Arg Leu Thr Lys
145                 150                 155                 160

Phe Leu Glu Gln Gln Met Gly Cys Arg Leu Asp Arg Pro
                165                 170


<210> SEQ ID NO 14
<211> LENGTH: 102
<212> TYPE: PRT
<213> ORGANISM: Arabidopsis thaliana

<400> SEQUENCE: 14

Met Ala Trp Ala Asp His Lys Lys Glu Ala Ala Trp Arg Leu Arg Arg
1               5                   10                  15

Leu Glu Leu Gln Leu Glu Ser Glu Lys Thr Cys Arg Gln Arg Glu Lys
            20                  25                  30

Met Glu Glu Ile Glu Ala Lys Met Lys Ala Leu Arg Glu Glu Gln Lys
        35                  40                  45

Asn Ala Met Glu Lys Ile Glu Gly Glu Tyr Arg Glu Gln Leu Val Gly
    50                  55                  60

Leu Arg Arg Asp Ala Glu Ala Lys Asp Gln Lys Leu Ala Asp Gln Trp
65                  70                  75                  80

Thr Ser Arg His Ile Arg Leu Thr Lys Phe Leu Glu Gln Gln Met Gly
                85                  90                  95

Cys Arg Leu Asp Arg Pro
            100


<210> SEQ ID NO 15
<211> LENGTH: 186
<212> TYPE: PRT
<213> ORGANISM: Gossypium arboreum

<400> SEQUENCE: 15

Met Trp Leu Ser Asn Ser Ser Asn Ala Ser Val Val Thr Pro Pro Ser
1               5                   10                  15

Pro Ser Val Thr Leu Ser Leu Ser Pro Ser Thr Val Ala Ala Ala Pro
            20                  25                  30

Pro Ile Pro Trp Leu Gln Pro Glu Arg Met Ser Glu Thr Ser Pro Val
        35                  40                  45

Leu Gly Asn Met Val Pro His Gly Ser Phe Pro Arg Ser Glu Asn Leu
    50                  55                  60

Leu Ile Ser Glu Leu Met Asp Cys Cys Arg Gln Leu Glu Asp Gly Arg
65                  70                  75                  80

Arg Ala Trp Val Ala His Arg Lys Glu Ala Ala Trp Arg Leu Arg Arg
                85                  90                  95
```

```
Val Glu Leu Gln Leu Glu Ser Glu Lys Ala Ser Arg Lys Arg Lys Lys
            100                 105                 110

Met Glu Glu Ile Glu Ser Lys Ile Glu Ala Leu Arg Glu Glu Gln Lys
        115                 120                 125

Ser Thr Leu Asp Arg Ile Glu Ala Glu Tyr Arg Glu Gln Leu Glu Gly
    130                 135                 140

Leu Arg Arg Asp Ala Glu Ala Lys Glu Gln Lys Leu Ala Glu Gln Trp
145                 150                 155                 160

Ala Ala Lys His Leu His Leu Thr Lys Phe Leu Glu Gln Thr Gly Cys
                165                 170                 175

Arg Pro Arg Val Val Glu Pro Asn Gly Gln
            180                 185


<210> SEQ ID NO 16
<211> LENGTH: 176
<212> TYPE: PRT
<213> ORGANISM: Gossypium arboreum

<400> SEQUENCE: 16

Met Val Thr Pro Pro Ser Pro Ser Val Thr Leu Ser Leu Ser Pro Ser
1               5                   10                  15

Thr Val Ala Ala Ala Pro Pro Ile Pro Trp Leu Gln Pro Glu Arg Met
            20                  25                  30

Ser Glu Thr Ser Pro Val Leu Gly Asn Met Val Pro His Gly Ser Phe
        35                  40                  45

Pro Arg Ser Glu Asn Leu Leu Ile Ser Glu Leu Met Asp Cys Cys Arg
    50                  55                  60

Gln Leu Glu Asp Gly Arg Arg Ala Trp Val Ala His Arg Lys Glu Ala
65                  70                  75                  80

Ala Trp Arg Leu Arg Arg Val Glu Leu Gln Leu Glu Ser Glu Lys Ala
                85                  90                  95

Ser Arg Lys Arg Lys Lys Met Glu Glu Ile Glu Ser Lys Ile Glu Ala
            100                 105                 110

Leu Arg Glu Glu Gln Lys Ser Thr Leu Asp Arg Ile Glu Ala Glu Tyr
        115                 120                 125

Arg Glu Gln Leu Glu Gly Leu Arg Arg Asp Ala Glu Ala Lys Glu Gln
    130                 135                 140

Lys Leu Ala Glu Gln Trp Ala Ala Lys His Leu His Leu Thr Lys Phe
145                 150                 155                 160

Leu Glu Gln Thr Gly Cys Arg Pro Arg Val Val Glu Pro Asn Gly Gln
                165                 170                 175


<210> SEQ ID NO 17
<211> LENGTH: 170
<212> TYPE: PRT
<213> ORGANISM: Gossypium arboreum

<400> SEQUENCE: 17

Met Ser Val Thr Leu Ser Leu Ser Pro Ser Thr Val Ala Ala Ala Pro
1               5                   10                  15

Pro Ile Pro Trp Leu Gln Pro Glu Arg Met Ser Glu Thr Ser Pro Val
            20                  25                  30

Leu Gly Asn Met Val Pro His Gly Ser Phe Pro Arg Ser Glu Asn Leu
        35                  40                  45

Leu Ile Ser Glu Leu Met Asp Cys Cys Arg Gln Leu Glu Asp Gly Arg
    50                  55                  60
```

```
Arg Ala Trp Val Ala His Arg Lys Glu Ala Ala Trp Arg Leu Arg Arg
65                  70                  75                  80

Val Glu Leu Gln Leu Glu Ser Glu Lys Ala Ser Arg Lys Arg Lys Lys
                85                  90                  95

Met Glu Glu Ile Glu Ser Lys Ile Glu Ala Leu Arg Glu Glu Gln Lys
            100                 105                 110

Ser Thr Leu Asp Arg Ile Glu Ala Glu Tyr Arg Glu Gln Leu Glu Gly
        115                 120                 125

Leu Arg Arg Asp Ala Glu Ala Lys Glu Gln Lys Leu Ala Glu Gln Trp
    130                 135                 140

Ala Ala Lys His Leu His Leu Thr Lys Phe Leu Glu Gln Thr Gly Cys
145                 150                 155                 160

Arg Pro Arg Val Val Glu Pro Asn Gly Gln
                165                 170


<210> SEQ ID NO 18
<211> LENGTH: 106
<212> TYPE: PRT
<213> ORGANISM: Gossypium arboreum

<400> SEQUENCE: 18

Met Ala Trp Val Ala His Arg Lys Glu Ala Ala Trp Arg Leu Arg Arg
1               5                   10                  15

Val Glu Leu Gln Leu Glu Ser Glu Lys Ala Ser Arg Lys Arg Lys Lys
            20                  25                  30

Met Glu Glu Ile Glu Ser Lys Ile Glu Ala Leu Arg Glu Glu Gln Lys
        35                  40                  45

Ser Thr Leu Asp Arg Ile Glu Ala Glu Tyr Arg Glu Gln Leu Glu Gly
    50                  55                  60

Leu Arg Arg Asp Ala Glu Ala Lys Glu Gln Lys Leu Ala Glu Gln Trp
65                  70                  75                  80

Ala Ala Lys His Leu His Leu Thr Lys Phe Leu Glu Gln Thr Gly Cys
                85                  90                  95

Arg Pro Arg Val Val Glu Pro Asn Gly Gln
            100                 105


<210> SEQ ID NO 19
<211> LENGTH: 26
<212> TYPE: DNA
<213> ORGANISM: Artificial Sequence
<220> FEATURE:
<223> OTHER INFORMATION: primer

<400> SEQUENCE: 19

accatgaagg agagacagcg gtggag                                          26


<210> SEQ ID NO 20
<211> LENGTH: 24
<212> TYPE: DNA
<213> ORGANISM: Artificial Sequence
<220> FEATURE:
<223> OTHER INFORMATION: primer

<400> SEQUENCE: 20

tcactgccca ttaggctcca caac                                            24


<210> SEQ ID NO 21
<211> LENGTH: 27
<212> TYPE: DNA
<213> ORGANISM: Artificial Sequence
```

<220> FEATURE:
<223> OTHER INFORMATION: primer

<400> SEQUENCE: 21
accatgaggg agaggcaacg gtggcga 27

<210> SEQ ID NO 22
<211> LENGTH: 29
<212> TYPE: DNA
<213> ORGANISM: Artificial Sequence
<220> FEATURE:
<223> OTHER INFORMATION: primer

<400> SEQUENCE: 22
ttagcggcca ccattaggtt ctgcaagtc 29

<210> SEQ ID NO 23
<211> LENGTH: 26
<212> TYPE: DNA
<213> ORGANISM: Artificial Sequence
<220> FEATURE:
<223> OTHER INFORMATION: primer

<400> SEQUENCE: 23
accatgaaag agagacaacg ttggag 26

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
tcaggggcgg tctaatctgc 20

<210> SEQ ID NO 25
<211> LENGTH: 26
<212> TYPE: DNA
<213> ORGANISM: Artificial Sequence
<220> FEATURE:
<223> OTHER INFORMATION: primer

<400> SEQUENCE: 25
accatgaaag ataggcaacg ttggag 26

<210> SEQ ID NO 26
<211> LENGTH: 24
<212> TYPE: DNA
<213> ORGANISM: Artificial Sequence
<220> FEATURE:
<223> OTHER INFORMATION: primer

<400> SEQUENCE: 26
ctatcttcca tttggttcag tgag 24

<210> SEQ ID NO 27
<211> LENGTH: 26
<212> TYPE: DNA
<213> ORGANISM: Artificial Sequence
<220> FEATURE:
<223> OTHER INFORMATION: primer

<400> SEQUENCE: 27
accatgaaag agagacaacg ttggag 26

<210> SEQ ID NO 28
<211> LENGTH: 24
<212> TYPE: DNA
<213> ORGANISM: Artificial Sequence
<220> FEATURE:
<223> OTHER INFORMATION: primer

<400> SEQUENCE: 28
tcagacaacg ttagaccgct cttt 24

<210> SEQ ID NO 29
<211> LENGTH: 26
<212> TYPE: DNA
<213> ORGANISM: Artificial Sequence
<220> FEATURE:
<223> OTHER INFORMATION: primer

<400> SEQUENCE: 29
accatgaaag agagacaacg ttggag 26

<210> SEQ ID NO 30
<211> LENGTH: 22
<212> TYPE: DNA
<213> ORGANISM: Artificial Sequence
<220> FEATURE:
<223> OTHER INFORMATION: primer

<400> SEQUENCE: 30
tcaaggcggg atcactgggt ta 22

<210> SEQ ID NO 31
<211> LENGTH: 32
<212> TYPE: DNA
<213> ORGANISM: Artificial Sequence
<220> FEATURE:
<223> OTHER INFORMATION: primer

<400> SEQUENCE: 31
accatgaagc aacagagaga agagaaagag ag 32

<210> SEQ ID NO 32
<211> LENGTH: 22
<212> TYPE: DNA
<213> ORGANISM: Artificial Sequence
<220> FEATURE:
<223> OTHER INFORMATION: primer

<400> SEQUENCE: 32
tcagaacaca ctctcgctac tc 22

<210> SEQ ID NO 33
<211> LENGTH: 33
<212> TYPE: DNA
<213> ORGANISM: Artificial Sequence
<220> FEATURE:
<223> OTHER INFORMATION: primer

<400> SEQUENCE: 33
accatgtggt tagctacttc taacaatggg aac 33

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
tcaggggcgg tctaatctgc 20

<210> SEQ ID NO 35
<211> LENGTH: 27
<212> TYPE: DNA
<213> ORGANISM: Artificial Sequence
<220> FEATURE:
<223> OTHER INFORMATION: primer

<400> SEQUENCE: 35
accatgaaga aagggtcttt gacagag 27

<210> SEQ ID NO 36
<211> LENGTH: 28
<212> TYPE: DNA
<213> ORGANISM: Artificial Sequence
<220> FEATURE:
<223> OTHER INFORMATION: primer

<400> SEQUENCE: 36
tcatcttagc ctccatgcag cctctttc 28

<210> SEQ ID NO 37
<211> LENGTH: 27
<212> TYPE: DNA
<213> ORGANISM: Artificial Sequence
<220> FEATURE:
<223> OTHER INFORMATION: primer

<400> SEQUENCE: 37
accatgaaga aagggtcttt gacagag 27

<210> SEQ ID NO 38
<211> LENGTH: 25
<212> TYPE: DNA
<213> ORGANISM: Artificial Sequence
<220> FEATURE:
<223> OTHER INFORMATION: primer

<400> SEQUENCE: 38
tcatctgtac tctccttcga tcttc 25

<210> SEQ ID NO 39
<211> LENGTH: 27
<212> TYPE: DNA
<213> ORGANISM: Artificial Sequence
<220> FEATURE:
<223> OTHER INFORMATION: primer

<400> SEQUENCE: 39
accatgaaga aagggtcttt gacagag 27

<210> SEQ ID NO 40
<211> LENGTH: 20
<212> TYPE: DNA
<213> ORGANISM: Artificial Sequence
<220> FEATURE:
<223> OTHER INFORMATION: primer

<400> SEQUENCE: 40
tcaggggcgg tctaatctgc 20

<210> SEQ ID NO 41

<211> LENGTH: 28
<212> TYPE: DNA
<213> ORGANISM: Artificial Sequence
<220> FEATURE:
<223> OTHER INFORMATION: primer

<400> SEQUENCE: 41
accatgcggt tagggaagtg gtgggaag 28

<210> SEQ ID NO 42
<211> LENGTH: 28
<212> TYPE: DNA
<213> ORGANISM: Artificial Sequence
<220> FEATURE:
<223> OTHER INFORMATION: primer

<400> SEQUENCE: 42
tcatcttagc ctccatgcag cctctttc 28

<210> SEQ ID NO 43
<211> LENGTH: 28
<212> TYPE: DNA
<213> ORGANISM: Artificial Sequence
<220> FEATURE:
<223> OTHER INFORMATION: primer

<400> SEQUENCE: 43
accatgcggt tagggaagtg gtgggaag 28

<210> SEQ ID NO 44
<211> LENGTH: 25
<212> TYPE: DNA
<213> ORGANISM: Artificial Sequence
<220> FEATURE:
<223> OTHER INFORMATION: primer

<400> SEQUENCE: 44
tcatctgtac tctccttcga tcttc 25

<210> SEQ ID NO 45
<211> LENGTH: 28
<212> TYPE: DNA
<213> ORGANISM: Artificial Sequence
<220> FEATURE:
<223> OTHER INFORMATION: primer

<400> SEQUENCE: 45
accatgcggt tagggaagtg gtgggaag 28

<210> SEQ ID NO 46
<211> LENGTH: 20
<212> TYPE: DNA
<213> ORGANISM: Artificial Sequence
<220> FEATURE:
<223> OTHER INFORMATION: primer

<400> SEQUENCE: 46
tcaggggcgg tctaatctgc 20

<210> SEQ ID NO 47
<211> LENGTH: 27
<212> TYPE: DNA
<213> ORGANISM: Artificial Sequence
<220> FEATURE:
<223> OTHER INFORMATION: primer

<400> SEQUENCE: 47
accatggcta attcgaatgg agggttt 27

<210> SEQ ID NO 48
<211> LENGTH: 20
<212> TYPE: DNA
<213> ORGANISM: Artificial Sequence
<220> FEATURE:
<223> OTHER INFORMATION: primer

<400> SEQUENCE: 48
tcaggggcgg tctaatctgc 20

<210> SEQ ID NO 49
<211> LENGTH: 26
<212> TYPE: DNA
<213> ORGANISM: Artificial Sequence
<220> FEATURE:
<223> OTHER INFORMATION: primer

<400> SEQUENCE: 49
accatggttg ttgcaaggcc tccctc 26

<210> SEQ ID NO 50
<211> LENGTH: 20
<212> TYPE: DNA
<213> ORGANISM: Artificial Sequence
<220> FEATURE:
<223> OTHER INFORMATION: primer

<400> SEQUENCE: 50
tcaggggcgg tctaatctgc 20

<210> SEQ ID NO 51
<211> LENGTH: 27
<212> TYPE: DNA
<213> ORGANISM: Artificial Sequence
<220> FEATURE:
<223> OTHER INFORMATION: primer

<400> SEQUENCE: 51
accatgtcgg taactttgac attatcg 27

<210> SEQ ID NO 52
<211> LENGTH: 20
<212> TYPE: DNA
<213> ORGANISM: Artificial Sequence
<220> FEATURE:
<223> OTHER INFORMATION: primer

<400> SEQUENCE: 52
tcaggggcgg tctaatctgc 20

<210> SEQ ID NO 53
<211> LENGTH: 24
<212> TYPE: DNA
<213> ORGANISM: Artificial Sequence
<220> FEATURE:
<223> OTHER INFORMATION: primer

<400> SEQUENCE: 53
accatggctt gggcagacca taag 24

<210> SEQ ID NO 54
<211> LENGTH: 20
<212> TYPE: DNA

<213> ORGANISM: Artificial Sequence
<220> FEATURE:
<223> OTHER INFORMATION: primer

<400> SEQUENCE: 54
tcaggggcgg tctaatctgc 20

<210> SEQ ID NO 55
<211> LENGTH: 33
<212> TYPE: DNA
<213> ORGANISM: Artificial Sequence
<220> FEATURE:
<223> OTHER INFORMATION: primer

<400> SEQUENCE: 55
accatgtggc tttctaattc cagcaatgca tcc 33

<210> SEQ ID NO 56
<211> LENGTH: 20
<212> TYPE: DNA
<213> ORGANISM: Artificial Sequence
<220> FEATURE:
<223> OTHER INFORMATION: primer

<400> SEQUENCE: 56
aggctccaca accctgggtc 20

<210> SEQ ID NO 57
<211> LENGTH: 26
<212> TYPE: DNA
<213> ORGANISM: Artificial Sequence
<220> FEATURE:
<223> OTHER INFORMATION: primer

<400> SEQUENCE: 57
accatggtca caccaccttc cccttc 26

<210> SEQ ID NO 58
<211> LENGTH: 20
<212> TYPE: DNA
<213> ORGANISM: Artificial Sequence
<220> FEATURE:
<223> OTHER INFORMATION: primer

<400> SEQUENCE: 58
aggctccaca accctgggtc 20

<210> SEQ ID NO 59
<211> LENGTH: 35
<212> TYPE: DNA
<213> ORGANISM: Artificial Sequence
<220> FEATURE:
<223> OTHER INFORMATION: primer

<400> SEQUENCE: 59
accatgtctg tgactttaag cttatctccc tcaac 35

<210> SEQ ID NO 60
<211> LENGTH: 20
<212> TYPE: DNA
<213> ORGANISM: Artificial Sequence
<220> FEATURE:
<223> OTHER INFORMATION: primer

<400> SEQUENCE: 60
aggctccaca accctgggtc 20

<210> SEQ ID NO 61
<211> LENGTH: 31
<212> TYPE: DNA
<213> ORGANISM: Artificial Sequence
<220> FEATURE:
<223> OTHER INFORMATION: primer

<400> SEQUENCE: 61
accatggctt gggttgcaca tagaaaggaa g 31

<210> SEQ ID NO 62
<211> LENGTH: 20
<212> TYPE: DNA
<213> ORGANISM: Artificial Sequence
<220> FEATURE:
<223> OTHER INFORMATION: primer

<400> SEQUENCE: 62
aggctccaca accctgggtc 20

<210> SEQ ID NO 63
<211> LENGTH: 33
<212> TYPE: DNA
<213> ORGANISM: Artificial Sequence
<220> FEATURE:
<223> OTHER INFORMATION: primer

<400> SEQUENCE: 63
accatgtggc tttctaattc cagcaatgca tcc 33

<210> SEQ ID NO 64
<211> LENGTH: 24
<212> TYPE: DNA
<213> ORGANISM: Artificial Sequence
<220> FEATURE:
<223> OTHER INFORMATION: primer

<400> SEQUENCE: 64
tcactgccca ttaggctcca caac 24

<210> SEQ ID NO 65
<211> LENGTH: 31
<212> TYPE: DNA
<213> ORGANISM: Artificial Sequence
<220> FEATURE:
<223> OTHER INFORMATION: primer

<400> SEQUENCE: 65
accatggctt gggttgcaca tagaaaggaa g 31

<210> SEQ ID NO 66
<211> LENGTH: 24
<212> TYPE: DNA
<213> ORGANISM: Artificial Sequence
<220> FEATURE:
<223> OTHER INFORMATION: primer

<400> SEQUENCE: 66
tcactgccca ttaggctcca caac 24

<210> SEQ ID NO 67
<211> LENGTH: 27
<212> TYPE: DNA
<213> ORGANISM: Artificial Sequence
<220> FEATURE:

<223> OTHER INFORMATION: primer

<400> SEQUENCE: 67
accatgacta tcaaatacaa caacatg 27

<210> SEQ ID NO 68
<211> LENGTH: 27
<212> TYPE: DNA
<213> ORGANISM: Artificial Sequence
<220> FEATURE:
<223> OTHER INFORMATION: primer

<400> SEQUENCE: 68
tcatacatct gaatttgtaa atacatc 27

<210> SEQ ID NO 69
<211> LENGTH: 20
<212> TYPE: DNA
<213> ORGANISM: Artificial Sequence
<220> FEATURE:
<223> OTHER INFORMATION: primer

<400> SEQUENCE: 69
accatgacaa cgagcggaac 20

<210> SEQ ID NO 70
<211> LENGTH: 28
<212> TYPE: DNA
<213> ORGANISM: Artificial Sequence
<220> FEATURE:
<223> OTHER INFORMATION: primer

<400> SEQUENCE: 70
ttaaacggtg aactttttat tgaatacg 28

<210> SEQ ID NO 71
<211> LENGTH: 367
<212> TYPE: PRT
<213> ORGANISM: Arabidopsis thaliana

<400> SEQUENCE: 71

```
Met Lys Glu Arg Gln Arg Trp Ser Gly Glu Glu Asp Ala Leu Leu Arg
1               5                   10                  15

Ala Tyr Val Arg Gln Phe Gly Pro Arg Glu Trp His Leu Val Ser Glu
            20                  25                  30

Arg Met Asn Lys Pro Leu Asn Arg Asp Ala Lys Ser Cys Leu Glu Arg
        35                  40                  45

Trp Lys Asn Tyr Leu Lys Pro Gly Ile Lys Lys Gly Ser Leu Thr Glu
    50                  55                  60

Glu Glu Gln Arg Leu Val Ile Arg Leu Gln Glu Lys His Gly Asn Lys
65                  70                  75                  80

Trp Lys Lys Ile Ala Ala Glu Val Pro Gly Arg Thr Ala Lys Arg Leu
                85                  90                  95

Gly Lys Trp Trp Glu Val Phe Lys Glu Lys Gln Gln Arg Glu Glu Lys
            100                 105                 110

Glu Ser Asn Lys Arg Val Glu Pro Ile Asp Glu Ser Lys Tyr Asp Arg
        115                 120                 125

Ile Leu Glu Ser Phe Ala Glu Lys Leu Val Lys Glu Arg Ser Asn Val
    130                 135                 140

Val Pro Ala Ala Ala Ala Ala Ala Thr Val Val Met Ala Asn Ser Asn
145                 150                 155                 160
```

```
Gly Gly Phe Leu His Ser Glu Gln Gln Val Gln Pro Pro Asn Pro Val
                165                 170                 175

Ile Pro Pro Trp Leu Ala Thr Ser Asn Asn Gly Asn Asn Val Val Ala
            180                 185                 190

Arg Pro Pro Ser Val Thr Leu Thr Leu Ser Pro Ser Thr Val Ala Ala
        195                 200                 205

Ala Ala Pro Gln Pro Pro Ile Pro Trp Leu Gln Gln Gln Gln Pro Glu
    210                 215                 220

Arg Ala Glu Asn Gly Pro Gly Gly Leu Val Leu Gly Ser Met Met Pro
225                 230                 235                 240

Ser Cys Ser Gly Ser Ser Glu Ser Val Phe Leu Ser Glu Leu Val Glu
                245                 250                 255

Cys Cys Arg Glu Leu Glu Glu Gly His Arg Ala Trp Ala Asp His Lys
            260                 265                 270

Lys Glu Ala Ala Trp Arg Leu Arg Arg Leu Glu Leu Gln Leu Glu Ser
        275                 280                 285

Glu Lys Thr Cys Arg Gln Arg Glu Lys Met Glu Glu Ile Glu Ala Lys
    290                 295                 300

Met Lys Ala Leu Arg Glu Glu Gln Lys Asn Ala Met Glu Lys Ile Glu
305                 310                 315                 320

Gly Glu Tyr Arg Glu Gln Leu Val Gly Leu Arg Arg Asp Ala Glu Ala
                325                 330                 335

Lys Asp Gln Lys Leu Ala Asp Gln Trp Thr Ser Arg His Ile Arg Leu
            340                 345                 350

Thr Lys Phe Leu Glu Gln Gln Met Gly Cys Arg Leu Asp Arg Pro
        355                 360                 365
```

<210> SEQ ID NO 72
<211> LENGTH: 21
<212> TYPE: DNA
<213> ORGANISM: Artificial Sequence
<220> FEATURE:
<223> OTHER INFORMATION: primer

<400> SEQUENCE: 72
ccgagagaat ggcatcttgt g 21

<210> SEQ ID NO 73
<211> LENGTH: 21
<212> TYPE: DNA
<213> ORGANISM: Artificial Sequence
<220> FEATURE:
<223> OTHER INFORMATION: primer

<400> SEQUENCE: 73
agaccctttc ttgatccctg g 21

<210> SEQ ID NO 74
<211> LENGTH: 21
<212> TYPE: DNA
<213> ORGANISM: Artificial Sequence
<220> FEATURE:
<223> OTHER INFORMATION: primer

<400> SEQUENCE: 74
ttatcgcctt ccacagtggc t 21

<210> SEQ ID NO 75
<211> LENGTH: 21

<212> TYPE: DNA
<213> ORGANISM: Artificial Sequence
<220> FEATURE:
<223> OTHER INFORMATION: primer

<400> SEQUENCE: 75
tcccactaca agacggcatc a 21

<210> SEQ ID NO 76
<211> LENGTH: 20
<212> TYPE: DNA
<213> ORGANISM: Artificial Sequence
<220> FEATURE:
<223> OTHER INFORMATION: primer

<400> SEQUENCE: 76
agccacaccg tcccaattta 20

<210> SEQ ID NO 77
<211> LENGTH: 21
<212> TYPE: DNA
<213> ORGANISM: Artificial Sequence
<220> FEATURE:
<223> OTHER INFORMATION: primer

<400> SEQUENCE: 77
cacgctcggt aaggatcttc a 21

<210> SEQ ID NO 78
<211> LENGTH: 183
<212> TYPE: PRT
<213> ORGANISM: Gossypium arboreum

<400> SEQUENCE: 78

```
Met Trp Leu Ser Asn Ser Ser Asn Ala Ser Val Val Thr Pro Pro Ser
1               5                   10                  15

Pro Ser Val Thr Leu Ser Leu Ser Pro Ser Thr Val Ala Ala Ala Pro
            20                  25                  30

Pro Ile Pro Trp Leu Gln Pro Glu Arg Met Ser Glu Thr Ser Pro Val
        35                  40                  45

Leu Gly Asn Met Val Pro His Gly Ser Phe Pro Arg Ser Glu Asn Leu
    50                  55                  60

Leu Ile Ser Glu Leu Met Asp Cys Cys Arg Gln Leu Glu Asp Gly Arg
65                  70                  75                  80

Arg Ala Trp Val Ala His Arg Lys Glu Ala Ala Trp Arg Leu Arg Arg
                85                  90                  95

Val Glu Leu Gln Leu Glu Ser Glu Lys Ala Ser Arg Lys Arg Lys Lys
            100                 105                 110

Met Glu Glu Ile Glu Ser Lys Ile Glu Ala Leu Arg Glu Glu Gln Lys
        115                 120                 125

Ser Thr Leu Asp Arg Ile Glu Ala Glu Tyr Arg Glu Gln Leu Glu Gly
    130                 135                 140

Leu Arg Arg Asp Ala Glu Ala Lys Glu Gln Lys Leu Ala Glu Gln Trp
145                 150                 155                 160

Ala Ala Lys His Leu His Leu Thr Lys Phe Leu Glu Gln Thr Gly Cys
                165                 170                 175

Arg Pro Arg Val Val Glu Pro
            180
```

<210> SEQ ID NO 79

```
<211> LENGTH: 173
<212> TYPE: PRT
<213> ORGANISM: Gossypium arboreum

<400> SEQUENCE: 79

Met Val Thr Pro Pro Ser Pro Ser Val Thr Leu Ser Leu Ser Pro Ser
1               5                   10                  15

Thr Val Ala Ala Ala Pro Pro Ile Pro Trp Leu Gln Pro Glu Arg Met
            20                  25                  30

Ser Glu Thr Ser Pro Val Leu Gly Asn Met Val Pro His Gly Ser Phe
        35                  40                  45

Pro Arg Ser Glu Asn Leu Leu Ile Ser Glu Leu Met Asp Cys Cys Arg
    50                  55                  60

Gln Leu Glu Asp Gly Arg Arg Ala Trp Val Ala His Arg Lys Glu Ala
65                  70                  75                  80

Ala Trp Arg Leu Arg Arg Val Glu Leu Gln Leu Glu Ser Glu Lys Ala
                85                  90                  95

Ser Arg Lys Arg Lys Lys Met Glu Glu Ile Glu Ser Lys Ile Glu Ala
            100                 105                 110

Leu Arg Glu Glu Gln Lys Ser Thr Leu Asp Arg Ile Glu Ala Glu Tyr
        115                 120                 125

Arg Glu Gln Leu Glu Gly Leu Arg Arg Asp Ala Glu Ala Lys Glu Gln
    130                 135                 140

Lys Leu Ala Glu Gln Trp Ala Ala Lys His Leu His Leu Thr Lys Phe
145                 150                 155                 160

Leu Glu Gln Thr Gly Cys Arg Pro Arg Val Val Glu Pro
                165                 170


<210> SEQ ID NO 80
<211> LENGTH: 167
<212> TYPE: PRT
<213> ORGANISM: Gossypium arboreum

<400> SEQUENCE: 80

Met Ser Val Thr Leu Ser Leu Ser Pro Ser Thr Val Ala Ala Ala Pro
1               5                   10                  15

Pro Ile Pro Trp Leu Gln Pro Glu Arg Met Ser Glu Thr Ser Pro Val
            20                  25                  30

Leu Gly Asn Met Val Pro His Gly Ser Phe Pro Arg Ser Glu Asn Leu
        35                  40                  45

Leu Ile Ser Glu Leu Met Asp Cys Cys Arg Gln Leu Glu Asp Gly Arg
    50                  55                  60

Arg Ala Trp Val Ala His Arg Lys Glu Ala Ala Trp Arg Leu Arg Arg
65                  70                  75                  80

Val Glu Leu Gln Leu Glu Ser Glu Lys Ala Ser Arg Lys Arg Lys Lys
                85                  90                  95

Met Glu Glu Ile Glu Ser Lys Ile Glu Ala Leu Arg Glu Glu Gln Lys
            100                 105                 110

Ser Thr Leu Asp Arg Ile Glu Ala Glu Tyr Arg Glu Gln Leu Glu Gly
        115                 120                 125

Leu Arg Arg Asp Ala Glu Ala Lys Glu Gln Lys Leu Ala Glu Gln Trp
    130                 135                 140

Ala Ala Lys His Leu His Leu Thr Lys Phe Leu Glu Gln Thr Gly Cys
145                 150                 155                 160

Arg Pro Arg Val Val Glu Pro
                165
```

```
<210> SEQ ID NO 81
<211> LENGTH: 103
<212> TYPE: PRT
<213> ORGANISM: Gossypium arboreum

<400> SEQUENCE: 81

Met Ala Trp Val Ala His Arg Lys Glu Ala Ala Trp Arg Leu Arg Arg
1               5                   10                  15

Val Glu Leu Gln Leu Glu Ser Glu Lys Ala Ser Arg Lys Arg Lys Lys
            20                  25                  30

Met Glu Glu Ile Glu Ser Lys Ile Glu Ala Leu Arg Glu Glu Gln Lys
        35                  40                  45

Ser Thr Leu Asp Arg Ile Glu Ala Glu Tyr Arg Glu Gln Leu Glu Gly
    50                  55                  60

Leu Arg Arg Asp Ala Glu Ala Lys Glu Gln Lys Leu Ala Glu Gln Trp
65                  70                  75                  80

Ala Ala Lys His Leu His Leu Thr Lys Phe Leu Glu Gln Thr Gly Cys
                85                  90                  95

Arg Pro Arg Val Val Glu Pro
            100


<210> SEQ ID NO 82
<211> LENGTH: 7
<212> TYPE: PRT
<213> ORGANISM: Unknown
<220> FEATURE:
<223> OTHER INFORMATION: Description of Unknown:
      Decoy peptide motif
<220> FEATURE:
<221> NAME/KEY: MOD_RES
<222> LOCATION: (6)..(6)
<223> OTHER INFORMATION: Ser or Thr

<400> SEQUENCE: 82

Pro Ser Val Thr Leu Xaa Leu
1               5
```